(12) United States Patent
Veiseh et al.

(10) Patent No.: US 12,697,300 B2
(45) Date of Patent: Aug. 4, 2026

(54) IMPLANTABLE CONSTRUCTS AND USES THEREOF

(71) Applicant: William Marsh Rice University, Houston, TX (US)

(72) Inventors: Omid Veiseh, Houston, TX (US); Amanda Nash, Houston, TX (US); Maria Isabel Jarvis-Ruocco, Houston, TX (US); Sudip Mukherjee, Houston, TX (US); Michael David Doerfert, Houston, TX (US); Samira Aghlara-Fotovat, Houston, TX (US); David Yu Zhang, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 1082 days.

(21) Appl. No.: 17/633,716

(22) PCT Filed: Aug. 7, 2020

(86) PCT No.: PCT/US2020/045471
§ 371 (c)(1),
(2) Date: Feb. 8, 2022

(87) PCT Pub. No.: WO2021/026484
PCT Pub. Date: Feb. 11, 2021

(65) Prior Publication Data
US 2022/0313599 A1 Oct. 6, 2022

Related U.S. Application Data

(60) Provisional application No. 63/012,693, filed on Apr. 20, 2020, provisional application No. 62/884,397, filed on Aug. 8, 2019.

(51) Int. Cl.
*A61K 9/00* (2006.01)
*A61K 45/06* (2006.01)

(52) U.S. Cl.
CPC ............ *A61K 9/0024* (2013.01); *A61K 45/06* (2013.01)

(58) Field of Classification Search
None
See application file for complete search history.

(56) References Cited

U.S. PATENT DOCUMENTS

2007/0071734 A1* 3/2007 Tao .................... A61K 48/0008
424/423
2008/0085295 A1* 4/2008 Melvik ................. A61L 24/001
424/195.17

FOREIGN PATENT DOCUMENTS

JP 2003524621 A 8/2003
WO WO-2019067766 A1 * 4/2019 ............. A61K 35/30

OTHER PUBLICATIONS

Hori, Yuki et al., "Injectable Dendritic Cell-Carrying Alginate Gels for Immunization and Immunotherapy", Sep. 30, 2008, pp. 3671-3682, vol. 29, No. 27, Biomaterials.
Zelante, Teresa et al., "Interleukin-2 Production by Dendritic Cells and Its Immuno-Regulatory Functions", Jun. 18, 2012, pp. 1-5, vol. 3, No. 161, Frontiers In Immunology.
Carreno, Beatriz M et al., "CD40 Regulates Human Dendritic Cell-Derived IL-7 Production That, In Turn, Contributes to CD8+ T-Cell Antigen-Specific Expansion", Nov. 11, 2008, pp. 167-177, vol. 87, Immunology and Cell Biology.
Wikstrom, Jonna et al., "Alginate-Based Microencapsulation of Retinal Pigment Epithelial Cell Line for Cell Therapy", Mar. 2008, pp. 869-876, vol. 29, Issue 7, Biomaterials.
International Search Report and Written Opinion for PCT Application No. PCT/US2020/045471 dated Nov. 2, 2020 (11 Pages).
Cameron, M.J. and Kelvin, D. J. Cytokines, Chemokines, and Their Receptors. From Madame Curie Bioscience Database [Internet], 25 pages (2013).
Hermanson, G. T. (ed). Bioconjugate Techniques, 3rd ed, Waltham, MA: Elsevier, Inc (2013).
Park, C. G. et al. Extended release of perioperative immunotherapy prevents tumor recurrence and eliminates metastases. Sci. Transl. Med 10(433), 14 pages (2018).

* cited by examiner

*Primary Examiner* — Celeste A Roney
(74) *Attorney, Agent, or Firm* — Baker, Donelson, Bearman, Caldwell & Berkowitz, PC

(57) ABSTRACT

The present disclosure relates to implantable constructs designed to deliver antigenic therapeutic reagents to a subject while providing protection from host immune responses. In certain aspects, the constructs are designed to degrade over time or upon a particular signal, thereby providing control of the length of time the therapeutic agent is delivered to the subject.

22 Claims, 13 Drawing Sheets

Specification includes a Sequence Listing.

FIGS. 1A-C

| | Control capsules | IL-2 secreting capsules |
|---|---|---|
| IP fluid | 0 | 2399 ± 137 |
| blood | 0 | 11 ± 6 |

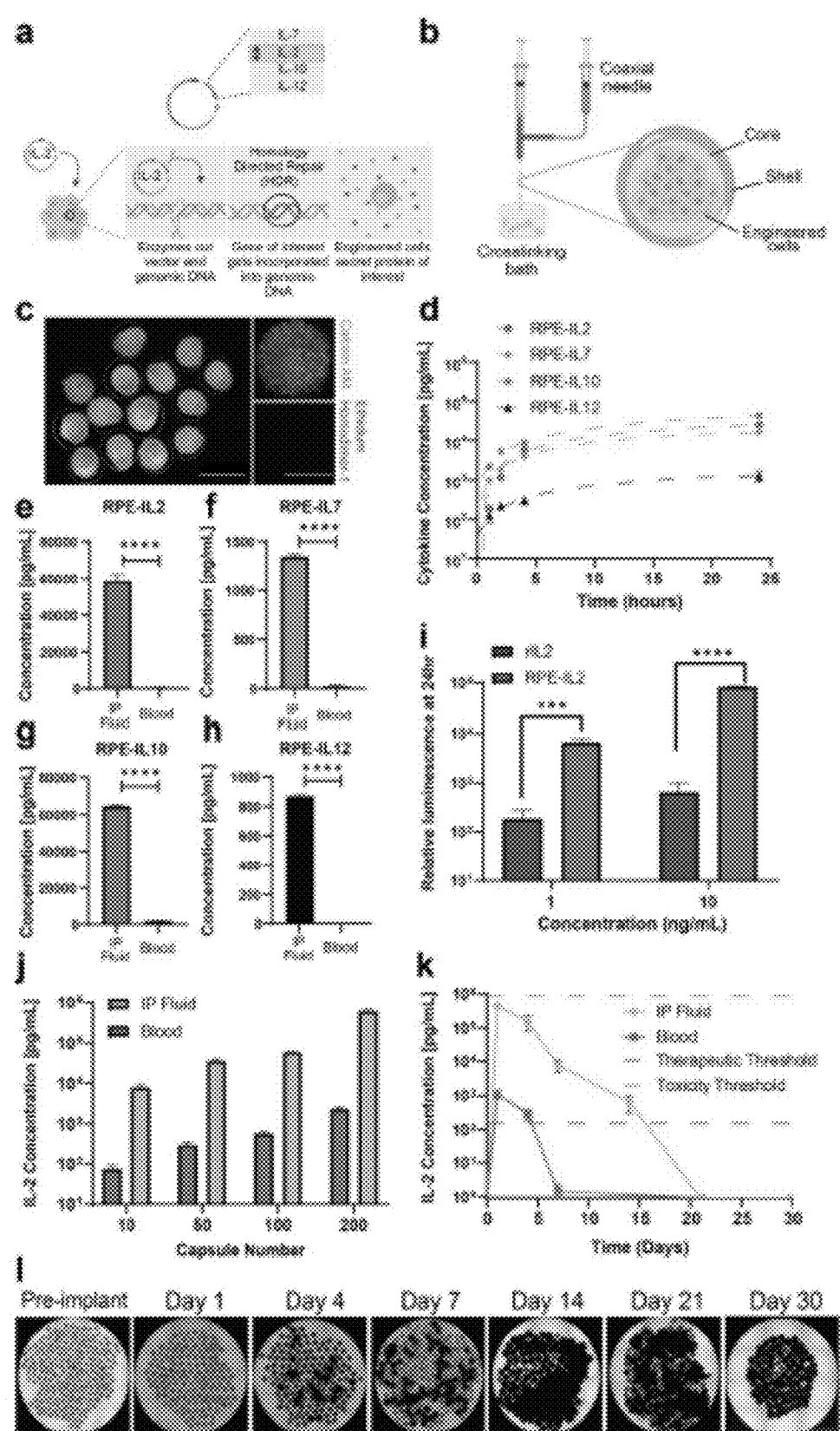
FIGS. 12A-L

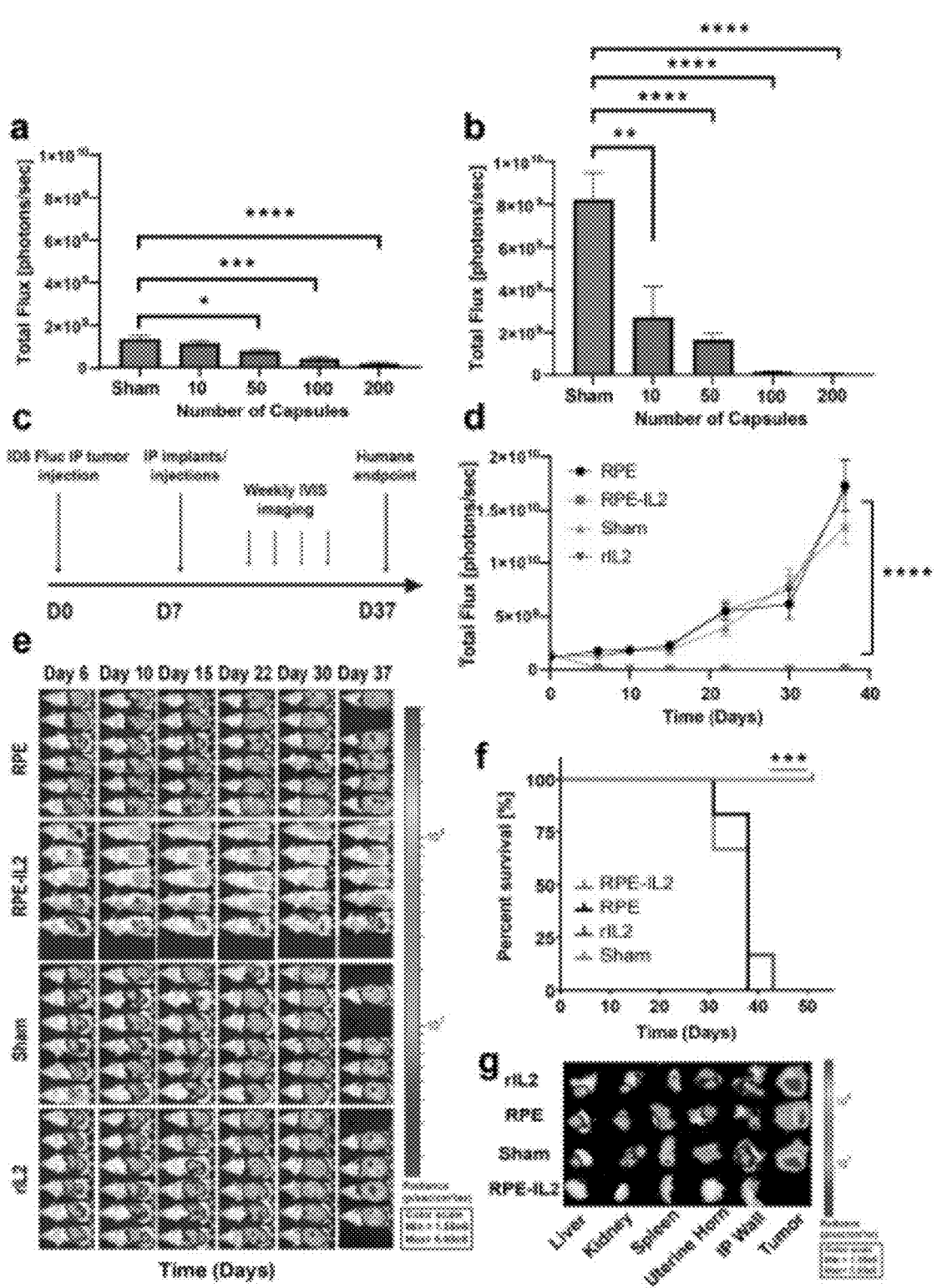
FIGS. 13A-G

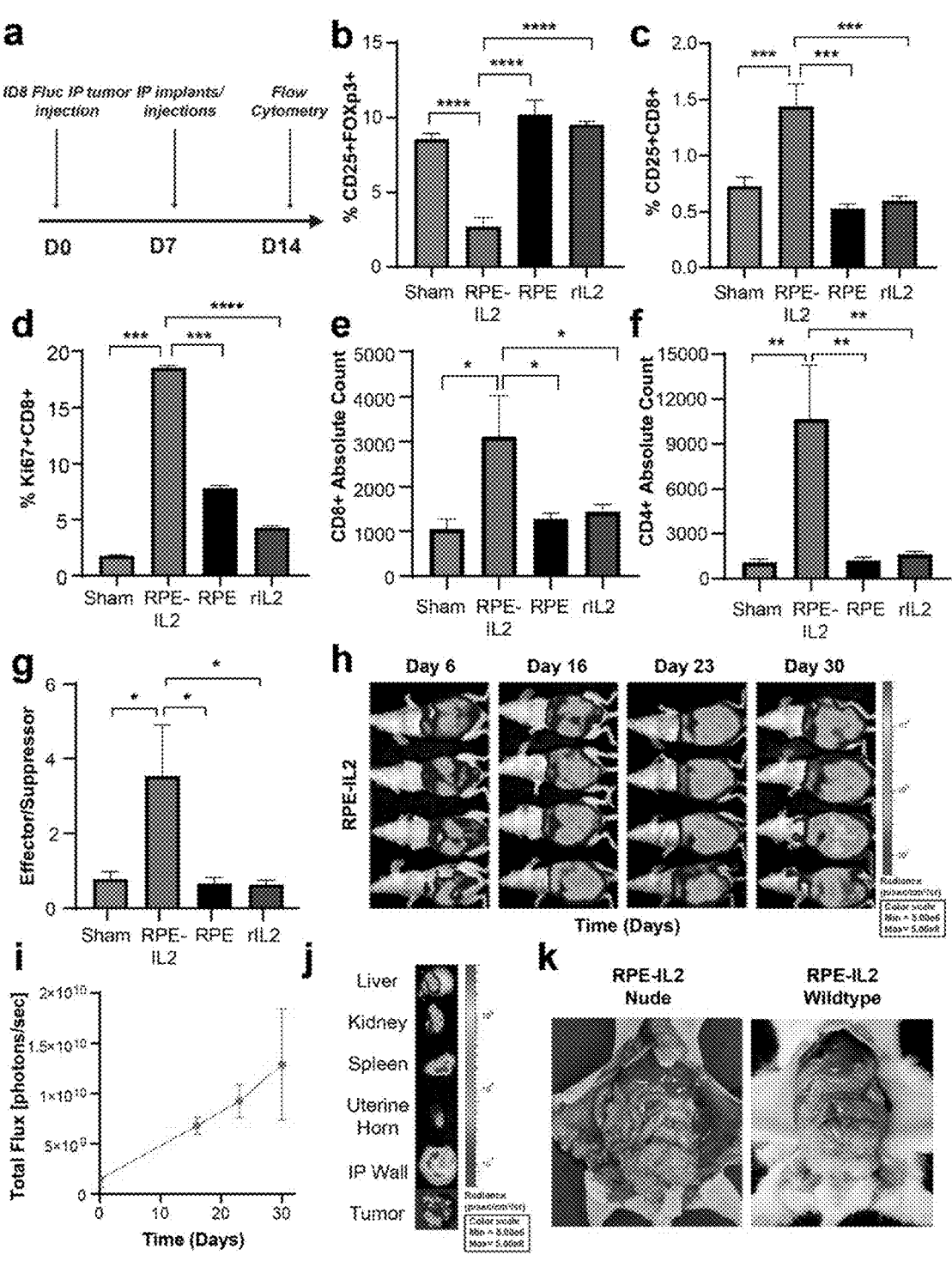
FIGS. 14A-K

SEQUENCE LISTING

```
<160> NUMBER OF SEQ ID NOS: 12

<210> SEQ ID NO 1
<211> LENGTH: 510
<212> TYPE: DNA
<213> ORGANISM: Artificial sequence
<220> FEATURE:
<223> OTHER INFORMATION: Synthetic oligonucleotide
```

```
<400> SEQUENCE: 1
atgtacagca tgcagctcgc atcctgtgtc acattgacac ttgtgctcct tgtcaacagc      60
gcacccactt caagctccac ttcaagctct acagcggaag cacagcagca gcagcagcag     120
cagcagcagc agcagcagca cctggagcag ctgttgatgg acctacagga gctcctgagc     180
aggatggaga attacaggaa cctgaaactc cccaggatgc tcaccttcaa attttacttg     240
cccaagcagg ccacagaatt gaaagatctt cagtgcctag aagatgaact tggacctctg     300
cggcatgttc tggatttgac tcaaagcaaa agctttcaat tggaagatgc tgagaatttc     360
atcagcaata tcagagtaac tgttgtaaaa ctaaagggct ctgacaacac atttgagtgc     420
caattcgatg atgagtcagc aactgtggtg gactttctga ggagatggat agccttctgt     480
caaagcatca tctcaacaag ccctcaataa                                     510

<210> SEQ ID NO 2
<211> LENGTH: 462
<212> TYPE: DNA
<213> ORGANISM: Artificial sequence
<220> FEATURE:
<223> OTHER INFORMATION: Synthetic oligonucleotide

<400> SEQUENCE: 2
atgtacagga tgcaactcct gtcttgcatt gcactaagtc ttgcacttgt cacaaacagt      60
gcacctactt caagttctac aaagaaaaca cagctacaac tggagcattt actgctggat     120
ttacagatga tttttgaatgg aattaataat tacaagaatc ccaaactcac caggatgctc     180
acatttaagt tttacatgcc caagaaggcc acagaactga aacatcttca gtgtctagaa     240
gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtgaata tgctgatgag acagcaacca ttgtagaatt tctgaacaga     420
tggattacct tttgtcaaag catcatctca acactgactt ga                      462

<210> SEQ ID NO 3
<211> LENGTH: 465
<212> TYPE: DNA
<213> ORGANISM: Artificial sequence
<220> FEATURE:
<223> OTHER INFORMATION: Synthetic oligonucleotide

<400> SEQUENCE: 3
atgttccatg tttctttag atatatcttt ggaattcctc cactgatcct tgttctgctg      60
cctgtcacat catctgagtg ccacattaaa gacaaagaag gtaaagcata tgagagtgta     120
ctgatgatca gcatcgatga attggacaaa atgacaggaa ctgatagtaa ttgcccgaat     180
aatgaaccaa acttttttag aaaacatgta tgtgatgata caaggaagc tgctttccta     240 aatcgtgctg ctcgcaagtt gaagcaattt cttaaaatga atatcagtga agaattcaat     300
gtccacttac taacagtatc acaggcaca caaacactgg tgaactgcac aagtaaggaa     360
gaaaaaaacg taaaggaaca gaaaaagaat gatgcatgtt tcctaaagag actactgaga     420
gaaataaaaa cttgttggaa taaaattttg aagggcagta tataa                    465

<210> SEQ ID NO 4
<211> LENGTH: 534
<212> TYPE: DNA
<213> ORGANISM: Artificial sequence
<220> FEATURE:
```

<223> OTHER INFORMATION: Synthetic oligonucleotide

<400> SEQUENCE: 4
atgttccatg tttcttttag gtatatcttt ggacttcctc ccctgatcct tgttctgttg      60
ccagtagcat catctgattg tgatattgaa ggtaaagatg gcaaacaata tgagagtgtt     120
ctaatggtca gcatcgatca attattggac agcatgaaag aaattggtag caattgcctg     180
aataatgaat ttaactttt taaaagacat atctgtgatg ctaataagga aggtatgttt      240
ttattccgtg ctgctcgcaa gttgaggcaa tttcttaaaa tgaatagcac tggtgatttt     300
gatctccact tattaaaagt ttcagaaggc acaacaatac tgttgaactg cactggccag     360
gttaaaggaa gaaaaccagc tgccctgggt gaagcccaac caacaaagag tttggaagaa     420
aataaatctt aaaggaaca gaaaaaactg aatgacttgt gtttcctaaa gagactatta      480
caagagataa aaacttgttg gaataaaatt ttgatgggca ctaaagaaca ctga           534

<210> SEQ ID NO 5
<211> LENGTH: 711
<212> TYPE: DNA
<213> ORGANISM: Artificial sequence
<220> FEATURE:
<223> OTHER INFORMATION: Synthetic oligonucleotide

<400> SEQUENCE: 5
atggtcagcg ttccaacagc ctcaccctcg gcatccagca gctcctctca gtgccggtcc      60
agcatgtgtc aatcacgcta cctcctcttt ttggccaccc ttgccctcct aaaccacctc     120
agtttggcca gggtcattcc agtctctgga cctgccaggt gtcttagcca gtcccgaaac     180
ctgctgaaga ccacagatga catggtgaag acggccagag aaaaactgaa acattattcc     240
tgcactgctg aagacatcga tcatgaagac atcacacggg accaaaccag cacattgaag     300
acctgtttac cactggaact acacaagaac gagagttgcc tggctactag agagacttct     360
tccacaacaa gagggagctg cctgccccca cagaagacgt ctttgatgat gaccctgtgc     420
cttggtagca tctatgagga cttgaagatg taccagacag agttccaggc catcaacgca     480
gcacttcaga atcacaacca tcagcagatc attctagaca aagggcatgct ggtggccatc     540 gatgagctga tgcagtctct gaatcataat ggcgagactc tgcgccagaa acctcctgtg     600
ggagaagcag acccttacag agtgaaaatg aagctctgca tcctgcttca cgccttcagc     660
acccgcgtcg tgaccatcaa cagggtgatg ggctatctga gctccgcctg a               711

<210> SEQ ID NO 6
<211> LENGTH: 1008
<212> TYPE: DNA
<213> ORGANISM: Artificial sequence
<220> FEATURE:
<223> OTHER INFORMATION: Synthetic oligonucleotide

<400> SEQUENCE: 6
atgtgtcctc agaagctaac catctcctgg tttgccatcg ttttgctggt gtctccactc      60
atggccatgt gggagctgga gaaagacgtt tatgttgtag aggtggactg gactcccgat     120
gcccctggag aaacagtgaa cctcacctgt gacacgcctg aagaagatga catcacctgg     180
acctcagacc agagacatgg agtcataggc tctggaaaga ccctgaccat cactgtcaaa     240
gagtttctag atgctggcca gtacacctgc cacaaaggag cgagactct gagccactca       300 catctgctgc tccacaagaa ggaaaatgga atttggtcca ctgaaatttt aaaaaatttc     360
aaaaacaaga ctttcctgaa gtgtgaagca ccaaattact ccggacggtt cacgtgctca     420

-continued

```
tggctggtgc aaagaaacat ggacttgaag ttcaacatca agagcagtag cagttcccct        480
gactctcggg cagtgacatg tggaatggcg tctctgtctg cagagaaggt cacactggac        540
caaagggact atgagaagta ttcagtgtcc tgccaggagg atgtcacctg cccaactgcc        600
gaggagaccc tgcccattga actggcgttg gaagcacggc agcagaataa atatgagaac        660
tacagcacca gcttcttcat cagggacatc atcaaaccag acccgcccaa gaacttgcag        720
atgaagcctt tgaagaactc acaggtggag gtcagctggg agtaccctga ctcctggagc        780
actccccatt cctacttctc cctcaagttc tttgttcgaa tccagcgcaa gaaagaaaag        840
atgaaggaga cagaggaggg gtgtaaccag aaaggtgcgt tcctcgtaga gaagacatct        900
accgaagtcc aatgcaaagg cgggaatgtc tgcgtgcaag ctcaggatcg ctattacaat        960
tcctcatgca gcaagtgggc atgtgttccc tgcagggtcc gatcctag               1008
```

<210> SEQ ID NO 7
<211> LENGTH: 762
<212> TYPE: DNA
<213> ORGANISM: Artificial sequence
<220> FEATURE:
<223> OTHER INFORMATION: Synthetic oligonucleotide

<400> SEQUENCE: 7

```
atgtggcccc ctgggtcagc ctcccagcca ccgccctcac ctgccgcggc cacaggtctg         60
catccagcgg ctcgccctgt gtccctgcag tgccggctca gcatgtgtcc agcgcgcagc        120
ctcctccttg tggctaccct ggtcctcctg gaccacctca gtttggccag aaacctcccc        180
gtggccactc cagacccagg aatgttccca tgccttcacc actcccaaaa cctgctgagg        240
gccgtcagca acatgctcca gaaggccaga caaactctag aattttaccc ttgcacttct        300
gaagagattg atcatgaaga tatcacaaaa gataaaacca gcacagtgga ggcctgttta        360
ccattggaat taaccaagaa tgagagttgc ctaaattcca gagagacctc tttcataact        420
aatgggagtt gcctggcctc cagaaagacc tcttttatga tggccctgtg ccttagtagt        480
atttatgaag acttgaagat gtaccaggtg gagttcaaga ccatgaatgc aaagcttctg        540
atggatccta gagaggcagat ctttctagat caaaacatgc tggcagttat tgatgagctg        600
atgcaggccc tgaatttcaa cagtgagact gtgccacaaa atcctccct tgaagaaccg        660 gattttata aaactaaaat caagctctgc atacttcttc atgctttcag aattcgggca        720
gtgactattg atagagtgat gagctatctg aatgcttcct aa                          762
```

<210> SEQ ID NO 8
<211> LENGTH: 987
<212> TYPE: DNA
<213> ORGANISM: Artificial sequence
<220> FEATURE:
<223> OTHER INFORMATION: Synthetic oligonucleotide

<400> SEQUENCE: 8

```
atgtgtcacc agcagttggt catctcttgg ttttccctgg tttttctggc atctcccctc         60
gtggccatat gggaactgaa gaaagatgtt tatgtcgtag aattggattg gtatccggat        120
gcccctggag aaatggtggt cctcacctgt gacacccctg aagaagatgg tatcacctgg        180
accttggacc agagcagtga ggtcttaggc tctggcaaaa ccctgaccat ccaagtcaaa        240
gagtttggag atgctggcca gtacacctgt cacaaaggag cggaggttct aagccattcg        300
ctcctgctgc ttcacaaaaaa ggaagatgga atttggtcca ctgatatttt aaaggaccag        360
```

-continued

```
aaagaaccca aaaataagac ctttctaaga tgcgaggcca agaattattc tggacgtttc      420
acctgctggt ggctgacgac aatcagtact gatttgacat tcagtgtcaa aagcagcaga      480
ggctcttctg acccccaagg ggtgacgtgc ggagctgcta cactctctgc agagagagtc      540
agaggggaca acaaggagta tgagtactca gtggagtgcc aggaggacag tgcctgccca      600
gctgctgagg agagtctgcc cattgaggtc atggtggatg ccgttcacaa gctcaagtat      660
gaaaactaca ccagcagctt cttcatcagg gacatcatca aacctgaccc acccaagaac      720
ttgcagctga agccattaaa gaattctcgg caggtggagg tcagctggga gtaccctgac      780
acctggagta ctccacattc ctacttctcc ctgacattct gcgttcaggt ccagggcaag      840
agcaagagag aaaagaaaga tagagtcttc acggacaaga cctcagccac ggtcatctgc      900
cgcaaaaatg ccagcattag cgtgcgggcc caggaccgct actatagctc atcttggagc      960
gaatgggcat ctgtgccctg cagttag                                         987
```

```
<210> SEQ ID NO 9
<211> LENGTH: 489
<212> TYPE: DNA
<213> ORGANISM: Artificial sequence
<220> FEATURE:
<223> OTHER INFORMATION: Synthetic oligonucleotide

<400> SEQUENCE: 9
atgaaaattt tgaaaccata tatgaggaat acatccatct cgtgctactt gtgtttcctt       60
ctaaacagtc actttttaac tgaggctggc attcatgtct tcattttggg ctgtgtcagt      120
gtaggtctcc ctaaaacaga ggccaactgg atagatgtaa gatatgacct ggagaaaatt      180
gaaagcctta ttcaatctat tcatattgac accactttat acactgacag tgactttcat      240
cccagttgca aagttactgc aatgaactgc tttctcctgg aattgcaggt tattttacat      300
gagtacagta acatgactct taatgaaaca gtaagaaacg tgctctacct tgcaaacagc      360
actctgtctt ctaacaagaa tgtagcagaa tctggctgca aggaatgtga ggagctggag      420
gagaaaacct tcacagagtt tttgcaaagc tttatacgca ttgtccaaat gttcatcaac      480
acgtcctga                                                             489
```

```
<210> SEQ ID NO 10
<211> LENGTH: 489
<212> TYPE: DNA
<213> ORGANISM: Artificial sequence
<220> FEATURE:
<223> OTHER INFORMATION: Synthetic oligonucleotide

<400> SEQUENCE: 10
atgagaattt cgaaaccaca tttgagaagt atttccatcc agtgctactt gtgtttactt       60
ctaaacagtc attttctaac tgaagctggc attcatgtct tcattttggg ctgtttcagt      120
gcagggcttc ctaaaacaga agccaactgg gtgaatgtaa taagtgattt gaaaaaaatt      180
gaagatctta ttcaatctat gcatattgat gctactttat atacggaaag tgatgttcac      240
cccagttgca aagtaacagc aatgaagtgc tttctcttgg agttacaagt tatttcactt      300
gagtccggag atgcaagtat tcatgataca gtagaaaatc tgatcatcct agcaaacaac      360
agtttgtctt ctaatgggaa tgtaacagaa tctggatgca aagaatgtga ggaactggag      420
gaaaaaaata ttaaagaatt tttgcagagt tttgtacata ttgtccaaat gttcatcaac      480
acttcttga                                                             489
```

```
<210> SEQ ID NO 11
<211> LENGTH: 1653
<212> TYPE: DNA
<213> ORGANISM: Artificial sequence
<220> FEATURE:
<223> OTHER INFORMATION: Synthetic oligonucleotide

<400> SEQUENCE: 11
atggaagacg ccaaaaacat aaagaaaggc ccggcgccat tctatccgct agaggatgga     60
accgctggag agcaactgca taaggctatg aagagatacg ccctggttcc tggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aaggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ctcctctgga    600
tctactgggt tacctaaggg tgtggccctt ccgcatagaa ctgcctgcgt cagattctcg    660
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttt tacgatccct tcaggattac    840
aaaattcaaa gtgcgttgct agtaccaacc ctattttcat tcttcgccaa aagcactctg    900
attgacaaat acgatttatc taatttacac gaaattgctt ctggggggcgc acctctttcg    960 aaagaagtcg gggaagcggt tgcaaaacgc ttccatcttc cagggatacg acaaggatat   1020
gggctcactg agactacatc agctattctg attacacccg aggggggatga taaaccgggc   1080 gcggtcggta aagttgttcc attttttgaa gcgaaggttg tggatctgga taccgggaaa   1140
acgctgggcg ttaatcagag aggcgaatta tgtgtcagag gacctatgat tatgtccggt   1200
tatgtaaaca atccggaagc gaccaacgcc ttgattgaca aggatggatg gctacattct   1260
ggagacatag cttactggga cgaagacgaa cacttcttca tagttgaccg cttgaagtct   1320
ttaattaaat acaaaggata ccaggtggcc cccgctgaat tggagtcgat attgttacaa   1380
caccccaaca tcttcgacgc gggcgtggca ggtcttcccg acgatgacgc cggtgaactt   1440
cccgccgccg ttgttgtttt ggagcacgga aagacgatga cggaaaaaga tcgtggat     1500 tacgtcgcca gtcaagtaac aaccgcgaaa aagttgcgcg gaggagttgt gtttgtggac   1560
gaagtaccga aaggtcttac cggaaaactc gacgcaagaa aaatcagaga gatcctcata   1620
aaggccaaga agggcggaaa gtccaaattg taa                                1653

<210> SEQ ID NO 12
<211> LENGTH: 660
<212> TYPE: DNA
<213> ORGANISM: Artificial sequence
<220> FEATURE:
<223> OTHER INFORMATION: Synthetic oligonucleotide

<400> SEQUENCE: 12
atggacatca aggtggtgtt caccctggtg ttcagcgccc tggtgcaggc caagagcacc     60
gagttcgacc ccaacatcga catcgtgggc ctggaaggca gttcggcat caccaacctg    120
```

-continued

```
gaaaccgacc tgttcaccat ctgggagacc atggaagtga tgatcaaggc cgacatcgcc    180
gacaccgacc gggccagcaa cttcgtggcc accgagaccg acgccaaccg gggcaagatg    240
cccggcaaga agctgcccct ggccgtcatc atggaaatgg aagccaacgc cttcaaggcc    300
ggctgcaccc ggggctgcct gatctgcctg agcaagatca agtgcaccgc caagatgaag    360
gtgtacatcc ccggcaggtg ccacgactac ggcggcgaca agaaaaccgg ccaggccggc    420
atcgtgggcg ccatcgtgga catccccgag atcagcggct tcaaagaaat ggcccccatg    480
gaacagttca tcgcccaggt ggacagatgc gccagctgca ccaccggctg cctgaagggc    540
ctggccaacg tgaagtgcag cgagctgctg aagaagtggc tgcccgaccg ctgcgccagc    600
ttcgccgaca agatccagaa agaggtgcac aacatcaagg gcatggccgg cgacaggtga    660
```

IMPLANTABLE CONSTRUCTS AND USES THEREOF

PRIORITY CLAIM

This application is a national phase application under 35 U.S.C. § 371 of International Application No. PCT/US2020/045471, filed Aug. 7, 2020, which claims benefit or priority to U.S. Provisional Application Ser. Nos. 62/884,397 and 63/012,693 filed Aug. 8, 2019 and Apr. 20, 2020, respectively, the entire contents of each application being hereby incorporated by reference.

STATEMENT REGARDING FEDERALLY FUNDED RESEARCH

This invention was made with government support under Grant No. R01DK120459, awarded by the National Institutes of Health. The government has certain rights in the invention.

BACKGROUND

I. Field

The present disclosure relates to the fields of biology, medicine, bioengineering and medicals devices. More particular, it relates to the development and use of implantable constructs designed to deliver antigenic therapeutic reagents to a subject and protect them from immune responses generated by the host. In particular, the constructs are designed to degrade over time or upon a particular signal, thereby providing control of the length of time the therapeutic agent is delivered to the subject.

II. Related Art

Advances in biomedical research have led to methods for localized and targeted therapies for the treatment of diseases, such as cancer. However, in many instances, the percentage of patients responsive to these approaches remain modest (Park et al., *Sci. Transl. Med.* 10(433) 2018).

One approach involves the use of implantable devices to deliver therapeutic agents. A fundamental barrier to successful device-based therapies is the lack of biocompatible transplantation devices. Implanted biomaterials lead to foreign body responses (FBRs), which are cascades of inflammatory events and wound-healing processes that lead to fibrosis (walling off) and subsequent implant failure. This response has been described for many materials, from naturally occurring polymers to synthetic materials. Thus, a critical medical need exists to develop biomaterials that overcome this key challenge of eliminating the FBR associated with biomaterial grafting. In addition, there is a need to control (i.e., down-regulate or stop) therapies after a period of time. At present, techniques for achieving the dual goals of FBR and controlled delivery of therapeutic agents are lacking.

Thus, there is a need for identifying new compositions and methods to enhance the delivery, distribution, and/or efficacy of therapeutic agents.

The development of this invention was funded in part by the Cancer Prevention and Research Institute of Texas under Grant No. RR160047.

SUMMARY

The present disclosure provides, at least in part, implantable constructs comprising an antigenic and/or a therapeutic agent useful for treating a disease in a subject, e.g., by enhancing the delivery and/or efficacy of the antigenic agent or therapeutic agent. The implantable constructs comprise a zone (e.g., a layer) to prevent contact of the antigenic agent and/or therapeutic agent from a host effector molecule, thereby shielding one or both from the host immune response.

Without wishing to be bound by theory, the implantable constructs disclosed herein may improve the efficacy of a therapeutic agent in a subject. In an embodiment, the implantable construct results in one or more of: (i) providing a controlled and sustained release of a therapeutic agent from the implantable construct; (ii) enabling local delivery of a therapeutic agent to yield systemic results; and (iii) modulating the activation and/or programming of a first host cell (e.g., a host effector T cell or a host NK cell) without activating or inducing expansion of a second host cell (e.g., a host T regulatory cell).

Certain embodiments described herein provide methods for the treatment or prevention of a disorder. In an embodiment, the disorder is a proliferative disorder, such as a cancer. These embodiments comprise administering to a subject an implantable construct described herein, e.g., comprising an antigenic and/or a therapeutic agent, for the treatment of the disease. The methods disclosed herein can result in a sustained release of a therapeutic agent at a target site (e.g., the intraperitoneal space), while having minimal or no effect at other non-target sites, thus avoiding the need for systemic delivery.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A and 1B show implanted capsules comprising RPE cells expressing only GFP (FIG. 1A) or GFP and IL-2 (FIG. 1B) immediately prior to implant in a mouse model. FIG. 1C depicts the implanted capsules expressing both GFP and IL-2 upon removal from the mouse model after 24 days of implant. The cells are image to show live cells (live) compared with dead cells (dead), and the two images are merged (merge).

FIG. 8D shows the overall tumor growth of the implanted mice from the study extending to 98 days, wherein mice implanted with encapsulated RPE cells expressing IL-2 (labeled "eRPE") exhibited tumor growth and elimination over the course of the study.

FIG. 9A shows images of implantable constructs comprising both an outer layer and an inner layer of variable thicknesses, where the outer layer is modified with FITC-dextran. The average thickness of each layer is controlled, e.g., by the flow rates of the materials during the encapsulation process. FIG. 9B is a chart showing the average outer layer thickness for each flow rate sample group shown in FIG. 9A: 0.02:0.2, 0.05:0.15, 0.1:0.1, 0.15: 0.05, 0.2:0.02 (p, 0.0001). FIG. 9C shows the degradability of a modified hyaluronic acid (NorHA) gel block (4 wt % NorHA, 10 mM peptide crosslinker, 0.05 wt % Irgacure 2959) over 1 hour in a solution of collagenase (10 mg/mL; top row) versus 1×PBS (bottom row). FIG. 9D is a graph plotting the data from FIG. 9C, showing the degradation behavior of the peptide-linked NorHA. The gel blocks were swelled in PBS overnight prior to the assay, and excess liquid was removed prior to weight measurement.

FIG. 10A is a general schematic depicting in vivo workflow for the MC38 colorectal model. FIG. 10B is a comparison of tumors collected from the i.p. space of euthanized mice (n=4 per group, C57ALB). FIG. 10C is a graph comparing the weight of collected tumors using an analytical balance and plotted per group as mean+/− SEM. FIG. 10D is a graph showing tumor weights normalized to the body weight of the animal at euthanasia. FIG. 10E is a schematic for a subcutaneous rechallenge study depicting a rechallenge occurring at Day 35 post initial injection. FIG. 10F is a graph showing the results of a rechallenge occurring at Day 7 after the first (n=3, C57ALB) Sham survival cohort reached humane endpoints. FIG. 10G are pictures comparing the visual differences in the tumor burdens of the Sham and control cohorts in the study outlined in the i.p. survival study (FIG. 10F). FIG. 10H is a graph showing the results of a rechallenge study, in which C57ALB mice (n=5) from the i.p. survival study (FIG. 10F) were rechallenged subcutaneously with MC38. Naïve controls (n=5) were also injected, and both groups were tracked over time and measured for tumor volume via caliper measurements.

FIG. 11A is a validation of the mouse model. FIG. 11B is a time-course image the cancer-infected albino mice in the presence or absence of the implantable construct after 6 days. Rainbow scale bar min 1.55e6, max 5e8 p/sec/cm$^2$.

FIGS. 12A-L. Development of encapsulated cells as cytokine factories with tuned in vivo pharmacokinetics. ARPE-19 cells were engineered using FIG. 12*a*) homology directed repair to create a portfolio of cytokine producing RPE cells expressing either human or mouse variants. FIG. 12*b*) Schematic of coaxial needle core-shell capsule production displaying engineering and production methods highlights design principles. FIG. 12*c*) 1.5 mm core-shell capsules containing naive RPE cells imaged after encapsulation in darkfield for visualization of translucent capsule surfaces (2×, Scale bar 2 um), and in fluorescence (4×, Scale bar 1 um) for viability qualitative analysis (GFP/Live, RFP, Dead). FIG. 12*d*) Post-encapsulation ELISA measurements of mouse cytokines IL2, IL7, IL10 & IL12 (n=4) display sustained release of cytokines (pg/mL, mean+/−SEM) from core-shell capsules after 4 hours, mouse cytokine expression levels (pg/mL) FIGS. 12*e-h*) measured at 24 hours post IP implantation (C57BL/6, 100 capsules) show extremely significant differences between protein concentration in local delivery sites (IP) versus systemic (blood) circulation (One-Way ANOVA, Holm-Sidak method, a=0.05, **p<0.0001). FIG. 12***i*) Relative luminescence of T Cells measured at 24 hours (n=8) after treatment with recombinant mouse IL2 and mouse IL2 secreted from RPE-IL2 core-shell capsules at two doses depicts dose dependent effects on proliferation of T Cells (*p<0.001 & p<0.0001) between groups. A Two-Way ANOVA, using the Holm-Sidak method for multiple comparisons was used. In vivo studies of RPE-IL2 capsules were conducted comparing secreted IL2 concentrations (pg/mL) in IP fluid versus plasma collected from blood j) as a function of discreet capsules doses (n=5 mice per group) at a fixed time point and FIG. 12***k*) as a function of time with a fixed dose of 200 capsules (n=5 mice per group). Values plotted are Mean+/− SEM. Therapeutic thresholds and toxicity thresholds were determined from reported literature values. Capsules collected from k) pharmacokinetic studies were imaged FIG. 12*l*) using brightfield microscopy (2×) to qualitatively monitor PFO of the alginate core-shell surface over time. Single field of view (2×) images with overlapping fields were stitched to create a multiarea high resolution image or mosaic.

FIGS. 13A-G. Native cytokine secreted from RPE-IL2 Core-Shell capsules have a significant effect in reducing tumor burden over time in ovarian cancer B6 Albino models.

ID8/MOSEC cells engineered to express Firefly Luciferase were tracked for growth in vivo and quantified using total flux (photons/sec) from luminescent measurements as a function of discreet capsule doses at fixed time points FIG. 13a) Day 6 (*p=0.01, *p=0.0002, p<0.0001) and FIG. 13b) Day 30 (p=0.001, **p<0.0001) plotted as Mean+/−SEM. One-Way ANOVA tests were used with the Holm-Sidak method for multiple comparisons of means across groups to determine significance. FIG. 13c) A schematic depicting the ovarian cancer study places injection of ID8/MOSEC at DO followed by implants (D7) and luminescent imaging schedules. FIG. 13d) Tracking of tumor burdens across groups (n=5-6) represented by total flux (photons/sec) of luminescent signal from ID8/MOSEC F-Luc expressing tumors plotted over time (days post implant, set at 0 on graph). Two-Way ANOVA, using the Holm-Sidak method for multiple comparisons test was used to determine significant between all groups and RPE-IL2 (p<0.0001), samples were plotted as Mean+/−SEM. FIG. 13e) Luminescent images of individual mice per group (n=5-6) were tracked over time and compiled for group comparisons (Panel d) total flux). Minima and Maxima average radiance (photons/sec/cm2/ser) represented by the rainbow scale bar were 5×10⁶ and 5×10⁸ respectively. FIG. 13f) Survival curves of all groups (n=5-6) depicted as percent survival over time in days post implantation showed statistically significant findings between RPE-IL2 and all other groups. The comparison of survival curves using the Log-Rank, Mantel-Cox test was used, *p=0.0009, by the Logrank test for trend **p=0.001. FIG. 13g) Organs collected from the IP space at humane endpoints were imaged for luminescent signal to determine presence of tumor nodules, visibly identifiable tumors were explanted and imaged alongside organs. Minima and maxima average radiances represented by the rainbow scale bar were 5×10⁶ and 5×10⁸ respectively (FIG. 13e and FIG. 13g) were collected using an f stop of 1.2, 15 seconds of exposure, and a field of view at 24 and 12 respectively.

FIGS. 14A-K. Immunological mechanistic insights of interleukin-12 on anti-tumor effects in vivo. FIG. 14a) A general schematic depicting animal model workflows supporting FIGS. 14b-g). At scientific endpoints all study groups (n=5–6) were plotted to show the FIG. 14b) percentage of CD25+FOXp3+ T Regulatory Cells as Frequency of Parent population (CD4+ T cells) **p<0.0001, FIG. 14c) the percentage of CD25+CD8+ Activated Cytotoxic T Cells as Frequency of Parent population (Broad Lymphocytes) *p=0.0004 (Sham v. RPE-IL2), *p=0.0002 (RPE-IL2 v. RPE or rIL2) FIG. 14d) the percentage of Ki67+CD8+ Proliferating Cytotoxic T Cells as a Frequency of Parent population (CD8+ T Cells) **p<0.0001, and the absolute counts of both FIG. 14e) CD8+ Cytotoxic T Cells *p=0.02 (Sham v RPE-IL2), *p=0.04 (RPE-IL2 v. RPE or rIL2) and FIG. 14f) of CD4+T Helper Cells within the entire population ***p=0.006. FIG. 14g) CD8+/CD4+CD25+ FOXp3+ or Effector versus Suppressor T cell ratios were plotted for all groups, *p=0.04. Ordinary One-way ANOVA were used with the Holm-Sidak method for multiple comparison's test to determine p values. FIG. 14h). Athymic female mice (n=4) injected with ID8/MOSEC FLuc and implanted with RPE-IL2 capsules were imaged over time for luminescent signal as an indicator of tumor burden, rainbow scale bar minima and maxima average radiance (photons/sec/cm2/ser) were 5×10⁶ and 5×10⁹ respectively (f stop 1.2, 3×3 smoothing, 1 binning, 15 second exposure, 24 field of view). FIG. 14i) Total Flux (photons/sec) were quantified from luminescent images acquired over time (FIG. 14h) and plotted as Mean+/−SEM. FIG. 14j) Representative organ images were selected for display at terminal endpoints (f stop 1.2, 4 binning, 15 seconds exposure, 12 field of view), FIG. 14k) necropsy images of organs & tumors in the IP space for athymic mice (NU/NU Nude, n=4) were photographed and compared to healthy mice (C57ALB, n=5).

DETAILED DESCRIPTION

Figure 1:
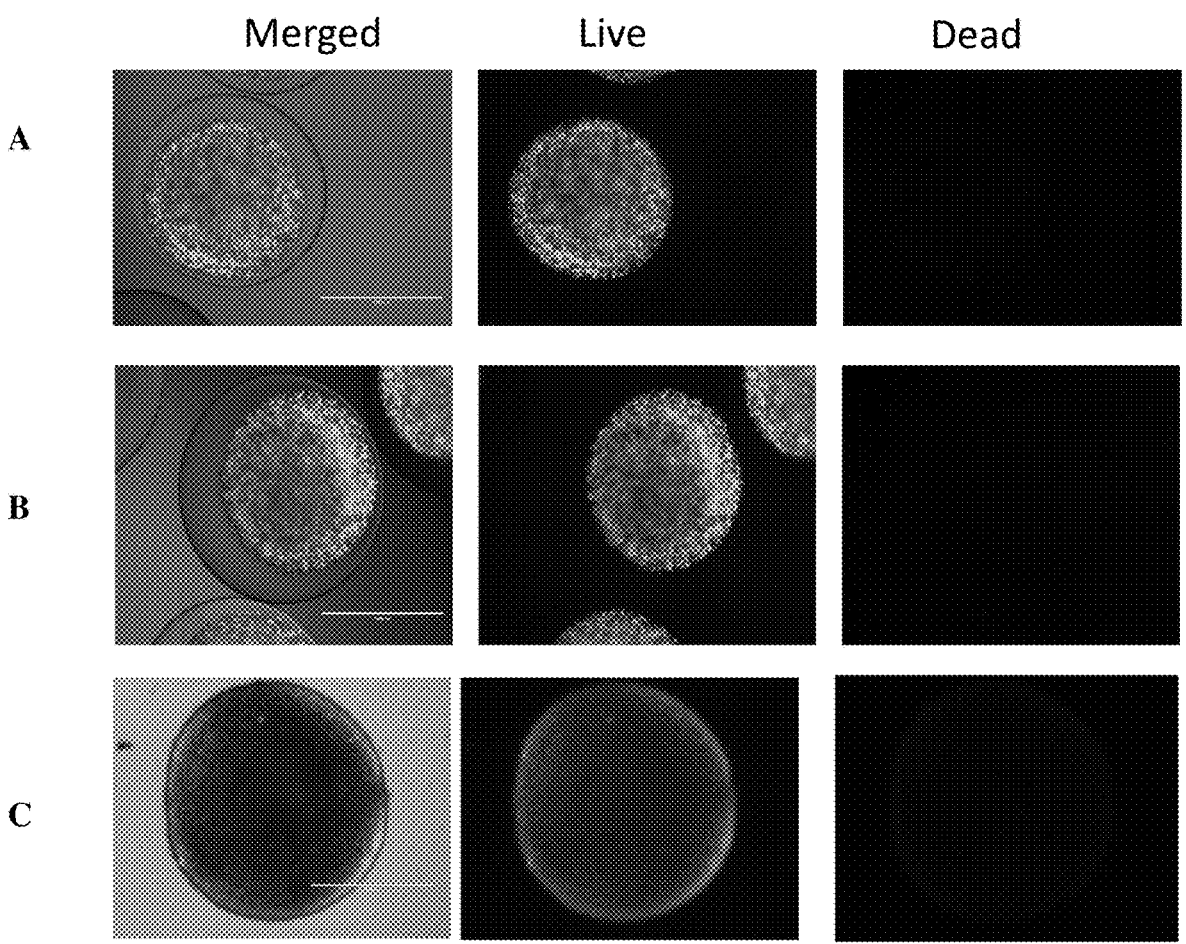
FIGS. 1A-C are images depicting exemplary implanted capsules comprising retinal pigment epithelial (RPE) cells transfected to express green fluorescent protein (GFP) alone or in combination with the cytokine IL-2.
Figure 2:
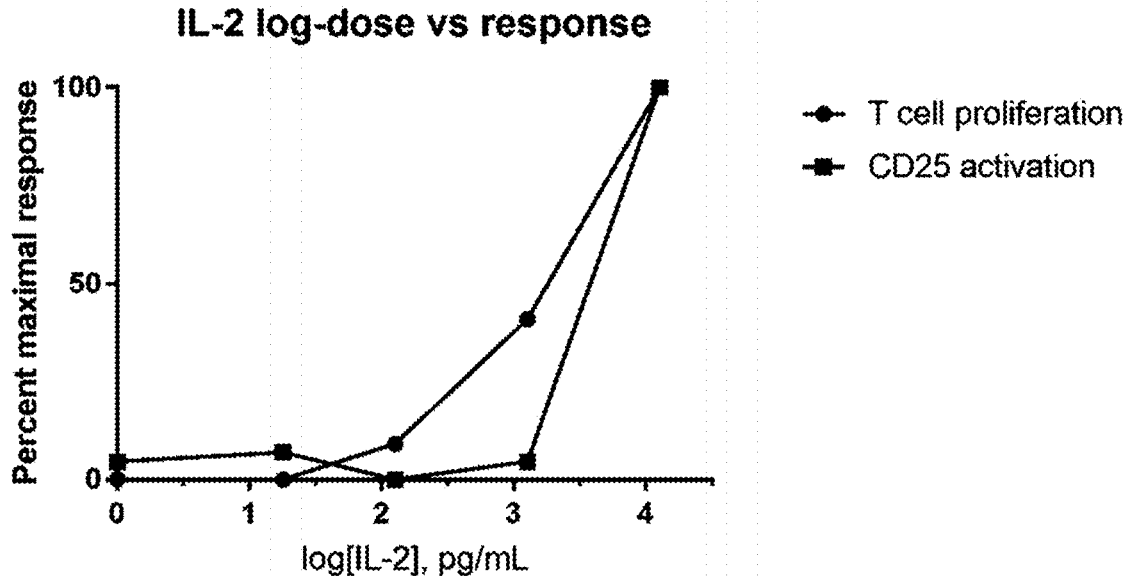
FIG. 2 is a graph indicating that secreted IL-2 from encapsulated RPE cells in vitro results in both T-cell proliferation and CD25 activation.
Figures 3A, 3B:
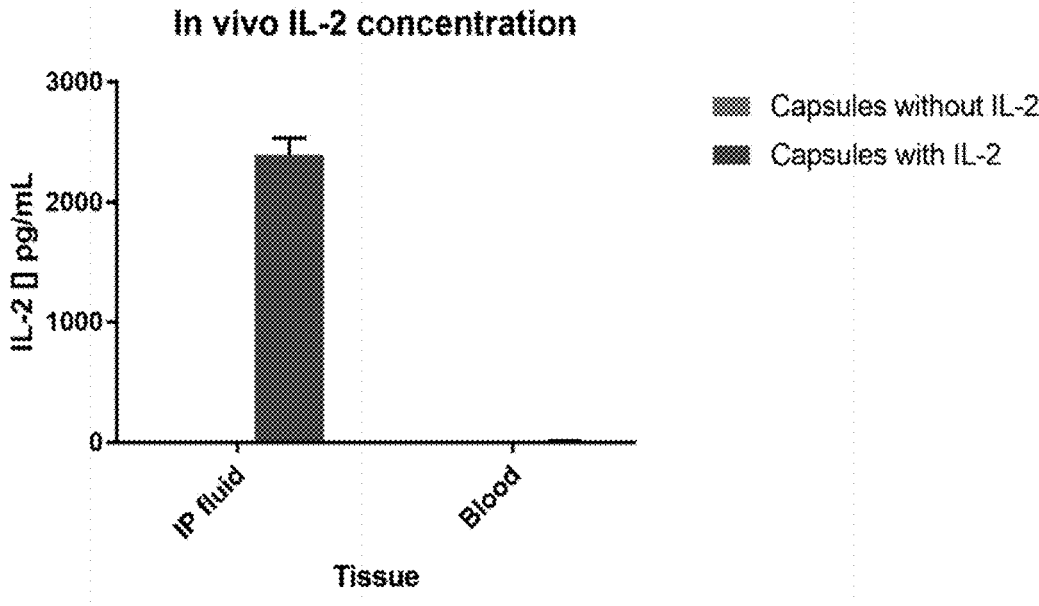
FIGS. 3A-B show the concentration of IL-2 (pg/mL) measured in a mouse model in either the intraperitoneal (IP) fluid or the blood, secreted from implanted capsules after 24 days of implantation in healthy mice.
Figure 4:
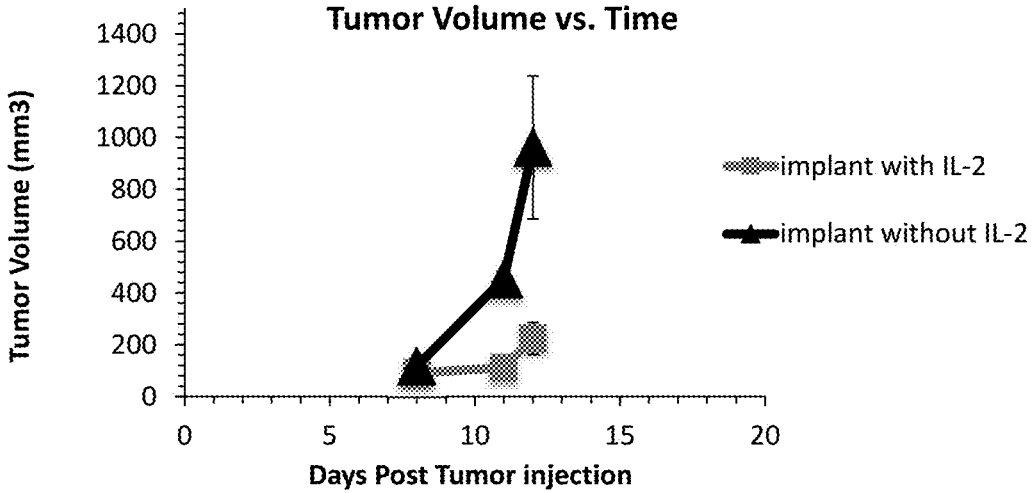
FIG. 4 is a graph showing a reduction in tumor size when exemplary capsules comprising RPE cells expressing IL-2 are implanted into a mouse melanoma tumor model.
Figure 5:
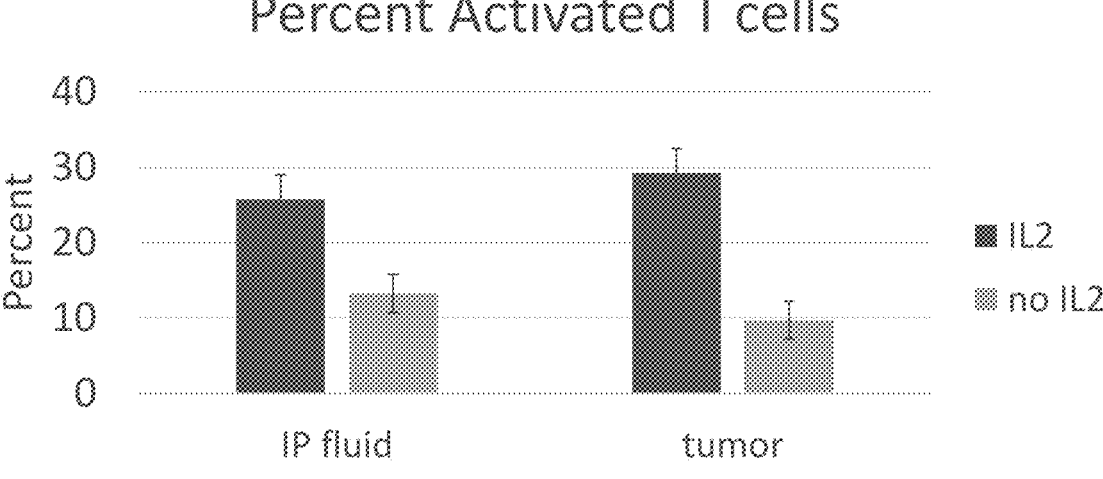
FIG. 5 is a graph depicting the percent increase in activated T cells (CD45+, CD3+, NK1.1, and CD25+) measured by flow cytometry in either the IP fluid or the tumor tissue in a mouse tumor model implanted with encapsulated cells expressing either IL-2 (blue bar) over a control (orange bar).
Figure 6:
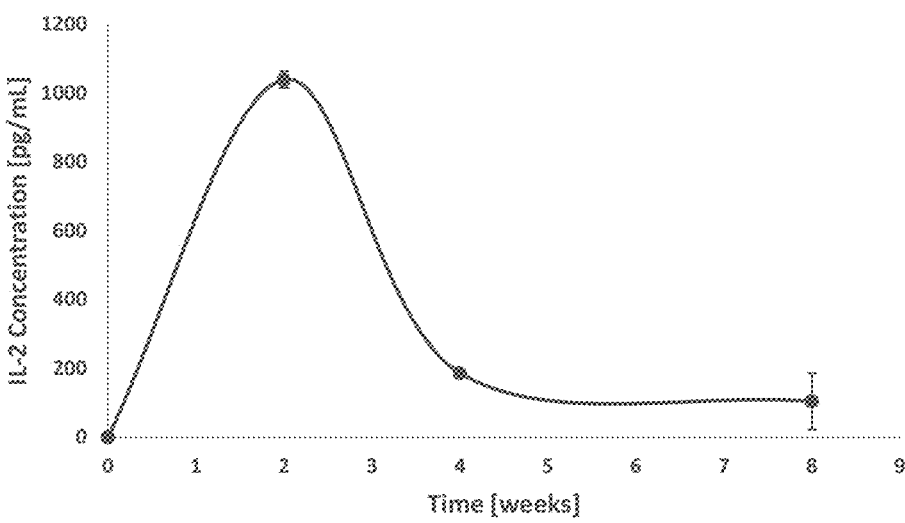
FIG. 6 is a time-course study done in healthy mice. This graph shows the change in IL-2 concentration in the IP fluid overtime. As shown in the graph, there is an increase in IL-2 concentration for two weeks, followed by a rapid decrease in concentration when IL-2 between 2- and 4-week time points.
Figure 7A:
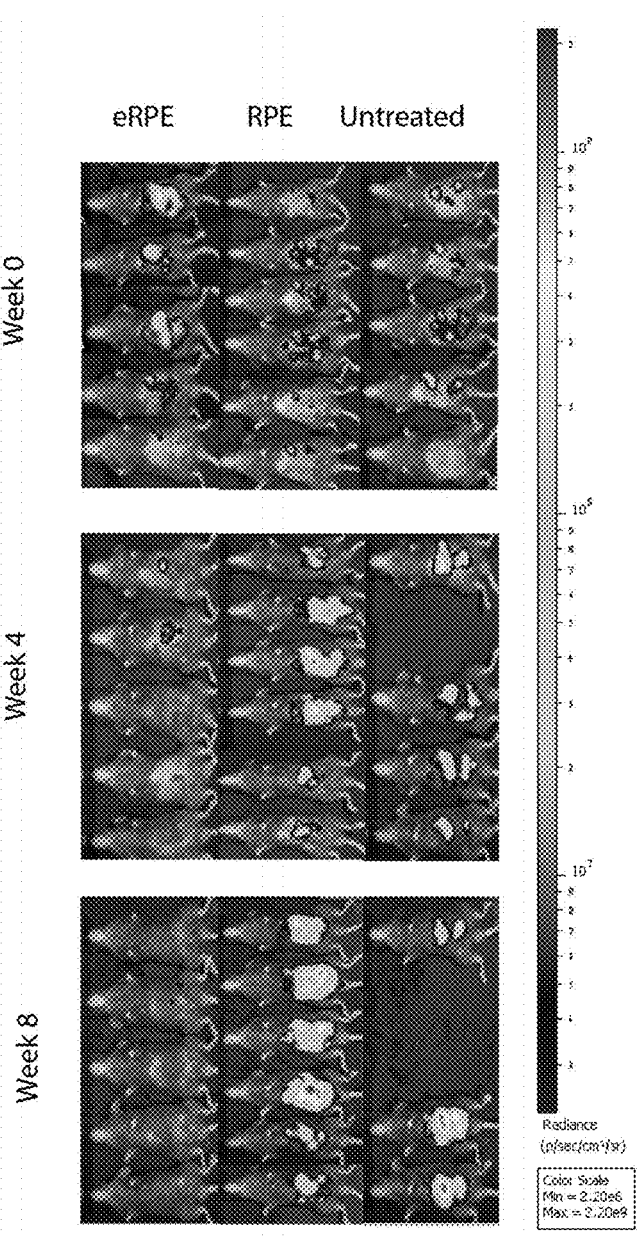
FIGS. 7A-7B depict the results of an experiment in which cohorts of a tumor-burdened mice were injected with either encapsulated RPE cells expressing IL-2, encapsulated RPE cells alone (no IL-2 expression), and untreated mice (FIG. 7A). The luminescence images reflect tumor size because the tumor cells have been engineered to express firefly luciferase and the mice were injected with luciferin substrate. Images were captured immediately after injection and daily for at least 65 days.
Figure 7B:
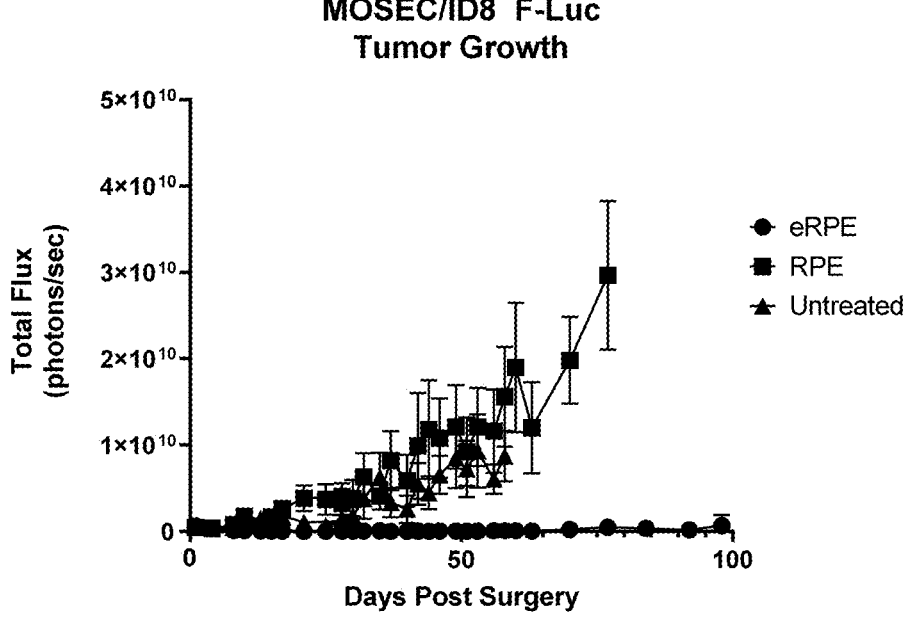
Figure 8:
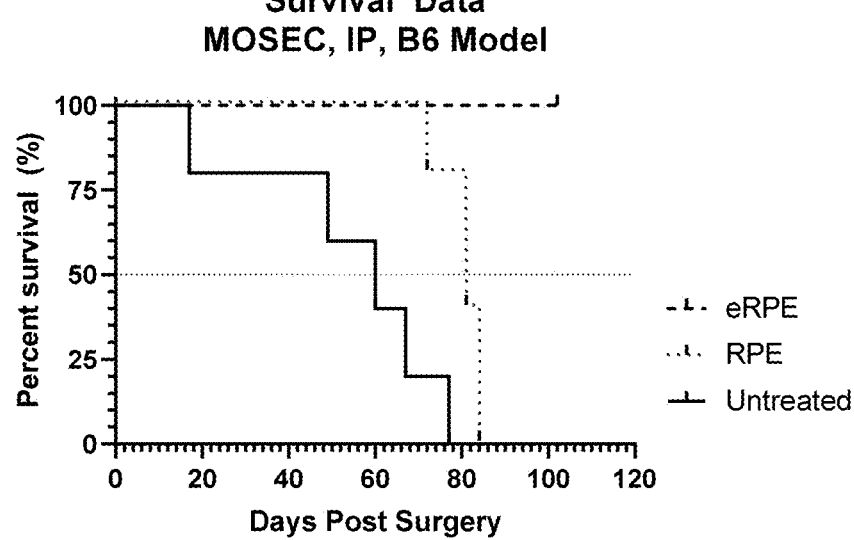
FIG. 8 is a survival curve summarizing the data from the experiments and data depicted in FIGS. 7A-7B. These graphs show that the tumor size in the mice decreased only in the cohort injected with encapsulated cells expressing IL-2 but did not change in either of the control cohorts.
Figures 9A, 9B, 9C, 9D:
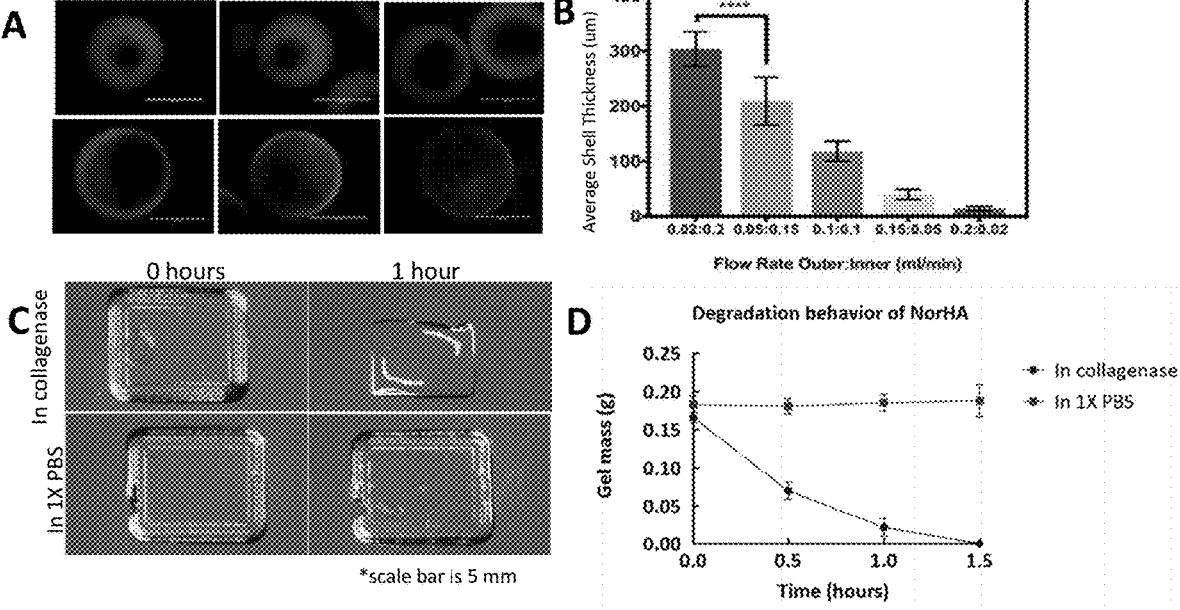
FIGS. 9A-9D depict exemplary implantable constructs and properties thereof.

The present disclosure features implantable constructs for delivery of an antigenic target (such as a cell and/or therapeutic agent) to a subject in a controlled release manner, and related methods of use thereof. The implantable constructs described herein comprise a zone (e.g., an inner zone or inner layer) that encapsulates the antigenic target, preventing contact of a host immune effector cell with the antigenic target to reduce immunoreactivity. In an embodiment, the zone is degradable, and allows for gradual removal of protection against the immune system in the case of encapsulated, therapy-producing cells or the gradual release of the antigenic target to the surrounding tissue or cells in the case where the antigenic target itself is intended for delivery. The implantable constructs disclosed herein may comprise a single zone or a plurality of zones, may be formulated into different morphologies (e.g., spheres, rods, tubes), and may be prepared using a variety of materials. Each of these embodiments will be described below in more detail.

I. Definitions

"Antigenic agent," as used herein, is a substance which induces, activates, or evokes an immune response, e.g., in a subject.

"Cell," as used herein, refers to an individual cell. In an embodiment, a cell is a primary cell or is derived from a cell culture. In an embodiment, a cell is a stem cell or is derived from a stem cell. A cell may be xenogeneic, autologous, or allogeneic. In an embodiment, a cell is be engineered (e.g., genetically engineered) or is not engineered (e.g., not genetically engineered).

"Degradable," as used herein, refers to a structure which upon modulation, e.g., cleavage, decreases the ability of the zone of the implantable construct (e.g., the inner zone and/or the outer zone) to impede contact of a host immune effector with the zone (e.g., the inner zone and/or the outer zone) or a component disposed in the zone. For example, the degradable entity can comprise a site which is cleavable by an enzyme, e.g., an endogenous host enzyme, or an administered enzyme. Typically, the degradable entity mediates a physical property of a zone, e.g., the inner zone or the outer zone, for example, the thickness, degree of cross-linking, or permeability, which impedes passage of a host agent (e.g., a host immune component, e.g., a host immune cell).

"Prevention," "prevent," and "preventing" as used herein refers to a treatment that comprises administering or applying a therapy, e.g., administering an implantable construct (e.g., as described herein) comprising a therapeutic agent (e.g., a therapeutic agent described herein) prior to the onset of a disease or condition in order to preclude the physical manifestation of said disease or condition. In some embodiments, "prevention," "prevent," and "preventing" require that signs or symptoms of the disease or condition have not yet developed or have not yet been observed. In some embodiments, treatment comprises prevention and in other embodiments it does not.

"Subject," as used herein, refers to the recipient of the implantable construct described herein. The subject may include a human and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development (e.g., a male or female of any age group, e.g., a pediatric subject (e.g., infant, child, adolescent) or adult subject (e.g., young adult, middle-aged adult, or senior adult). A non-human animal may be a transgenic animal.

"Treatment," "treat," and "treating," as used herein, refer to reversing, alleviating, delaying the onset of, or inhibiting the progress of one or more of a symptom, manifestation, or underlying cause of a disease or condition. (e.g., as described herein), e.g., by administering or applying a therapy, e.g., administering an implantable construct comprising a therapeutic agent (e.g., a therapeutic agent described herein). In an embodiment, treating comprises reducing, reversing, alleviating, delaying the onset of, or inhibiting the progress of a symptom of a disease, disorder, or condition. In an embodiment, treating comprises reducing, reversing, alleviating, delaying the onset of, or inhibiting the progress of a manifestation of a disease or condition. In an embodiment, treating comprises reducing, reversing, alleviating, reducing, or delaying the onset of, an underlying cause of a disease or condition. In some embodiments, "treatment," "treat," and "treating" require that signs or symptoms of the disease or condition have developed or have been observed. In other embodiments, treatment may be administered in the absence of signs or symptoms of the disease or condition, e.g., in preventive treatment. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence. Treatment may also be continued after symptoms have resolved, for example, to delay or prevent recurrence. In some embodiments, treatment comprises prevention and in other embodiments it does not.

A. IMPLANTABLE CONSTRUCTS

An implantable construct described herein comprises a material that reduces or inhibits a reaction (e.g., such as an immunomodulatory reaction) with or on an antigenic or therapeutic agent disposed within. For example, an implantable construct comprises a zone or layer that shields an antigenic agent from exposure to the surrounding milieu, such as host tissue, host cells, or host cell products. In an embodiment, an implantable construct minimizes the effect of a host response (e.g., an immune response) directed at an antigenic or therapeutic agent disposed within, e.g., as compared with a similar antigenic agent that is not disposed within an implantable construct.

The implantable construct may comprise a permeable, semi-permeable, or impermeable material to control the flow of solution in and out of the implantable construct. For example, the material may be permeable or semi-permeable to allow free passage of small molecules, such as nutrients and waste products, in and out of the construct. In addition, the material may be permeable or semi-permeable to allow the transport of an antigenic or therapeutic agent, out of the implantable construct. Exemplary materials include polymers, metals, ceramics, and combinations thereof.

In an embodiment, the implantable construct comprises a polymer (e.g., a naturally occurring polymer or a synthetic polymer). For example, a polymer may comprise polystyrene, polyester, polycarbonate, polyethylene, polypropylene, polyfluorocarbon, nylon, polyacetylene, polyvinyl chloride (PVC), polyolefin, polyurethane, polyacrylate, polymethacrylate, polyacrylamide, polymethacrylamide, polymethyl methacrylate, poly(2-hydroxyethyl methacrylate), polysiloxane, polydimethylsiloxane (PDMS), polyhydroxyalkanoate, PEEK®, polytetrafluoroethylene, polyethylene glycol, polysulfone, polyacrylonitrile, collagen, cellulose, cellulosic polymers, polysaccharides, polyglycolic acid, poly(L-lactic acid) (PLLA), poly(lactic glycolic acid) (PLGA), polydioxanone (PDA), poly(lactic acid), hyaluronic acid, agarose, alginate, chitosan, or a blend or copolymer thereof. In an embodiment, the implantable construct comprises a polysaccharide (e.g., alginate, cellulose, hyaluronic acid, or chitosan). In an embodiment, the implantable construct comprises hyaluronic acid. In an embodiment, the implantable construct comprises alginate. In some embodiments, the average molecular weight of the polymer is from about 2 kDa to about 500 kDa (e.g., from about 2.5 kDa to about 175 kDa, from about 5 kDa about 150 kDa, from about 10 kDa to about 125 kDa, from about 12.5 kDa to about 100 kDa, from about 15 kDa to about 90 kDa, from about 17.5 kDa to about about 80 kDa, from about 20 kDa to about 70 kDa, from about 22.5 kDa to about 60 kDa, or from about 25 kDa to about 50 kDa). The implantable construct may comprise at least 0.5%, 1%, 2%, 3%, 4%, 5%, 7.5%, 10%, 15%, 20%, 30%, 40%, 50%, 60%, 70%, 80% or more of a polymer, e.g., a polymer described herein.

In an embodiment, the implantable construct comprises a polysaccharide, e.g., hyaluronic acid or an alginate. Alginate is a naturally occurring polymer comprising $\beta$-(1-4)-linked mannuronic acid and guluronic acid residues, and as a result of its high density of negatively charged carboxylates, may be cross-linked with certain cations to form a larger structure, such as a hydrogel. Alginate polymers described herein may have an average molecular weight from about 2 kDa to about 500 kDa (e.g., from about 2.5 kDa to about 175 kDa, from about 5 kDa about 150 kDa, from about 10 kDa to about 125 kDa, from about 12.5 kDa to about 100 kDa, from about 15 kDa to about 90 kDa, from about 17.5 kDa to about about 80 kDa, from about 20 kDa to about 70 kDa, from about 22.5 kDa to about 60 kDa, or from about 25 kDa to about 50 kDa). In an embodiment, the implantable construct comprises at least 0.5%, 1%, 2%, 3%, 4%, 5%, 7.5%, 10%, 15%, 20%, 30%, 40%, 50%, 60%, 70%, 80% or more of an alginate polymer. In an embodiment, the alginate is an ultrapure alginate (e.g., SLG20 alginate).

In an embodiment, the implantable construct comprises a metal or a metallic alloy. Exemplary metals or metallic alloys include titanium (e.g., nitinol, nickel titanium alloys, thermo-memory alloy materials), platinum, platinum group alloys, stainless steel, tantalum, palladium, zirconium, niobium, molybdenum, nickel-chrome, cobalt, tantalum, chromium molybdenum alloys, nickel-titanium alloys, and cobalt chromium alloys. In an embodiment, the implantable construct comprises stainless steel grade. The implantable construct may comprise at least 0.5%, 1%, 2%, 3%, 4%, 5%, 7.5%, 10%, 15%, 20%, 30%, 40%, 50%, 60%, 70%, 80% or more of a metal or metallic alloy, e.g., a metal or metallic alloy described herein.

In an embodiment, the implantable construct comprises a ceramic. Exemplary ceramics include a carbide, nitride, silica, or oxide materials (e.g., titanium oxides, hafnium oxides, iridium oxides, chromium oxides, aluminum oxides, and zirconium oxides). The implantable construct may comprise at least 0.5%, 1%, 2%, 3%, 4%, 5%, 7.5%, 10%, 15%, 20%, 30%, 40%, 50%, 60%, 70%, 80% or more of a ceramic, e.g., a ceramic described herein.

In an embodiment, the implantable construct may comprise glass. The implantable construct may comprise at least 0.5%, 1%, 2%, 3%, 4%, 5%, 7.5%, 10%, 15%, 20%, 30%, 40%, 50%, 60%, 70%, 80% or more glass.

A material within an implantable construct may be further modified, for example, with a chemical modification. For example, a material may be coated or derivatized with a chemical modification that provides a specific feature, such as an immunomodulatory or antifibrotic feature. Exemplary chemical modifications include small molecules, peptides, proteins, nucleic acids, lipids, or oligosaccharides. The implantable construct may comprise at least 0.5%, 1%, 2%, 3%, 4%, 5%, 7.5%, 10%, 15%, 20%, 30%, 40%, 50%, 60%, 70%, 80% or more of a material that is chemically modified, e.g., with a chemical modification described herein.

In some embodiments, the material is chemically modified with a specific density of modifications. The specific density of chemical modifications may be described as the average number of attached chemical modifications per given area. For example, the density of a chemical modification on a material in, on, or within an implantable construct described herein may be 0.01, 0.1, 0.5, 1, 5, 10, 15, 20, 50, 75, 100, 200, 400, 500, 750, 1,000, 2,500, or 5,000 chemical modifications per square μm or square mm.

In an embodiment, the chemical modification of a material may include a linker or other attachment moiety. These linkers may include a cross-linker, an amine-containing linker, an ester-containing linker, a photolabile linker, a peptide-containing linker, a disulfide-containing linker, an amide-containing linker, a phosphoryl-containing linker, or a combination thereof. A linker may be labile (e.g., hydrolysable). Exemplary linkers or other attachment moieties is summarized in *Bioconjugate Techniques* (3$^{rd}$ ed, Greg T. Hermanson, Waltham, MA: Elsevier, Inc, 2013), which is incorporated herein by reference in its entirety.

B. CELLS

Implantable constructs described herein may contain a cell, for example, an engineered cell. A cell be derived from any mammalian organ or tissue, including the brain, nerves, ganglia, spine, eye, heart, liver, kidney, lung, spleen, bone, thymus, lymphatic system, skin, muscle, pancreas, stomach, intestine, blood, ovary, uterus, or testes.

A cell may be derived from a donor (e.g., an allogeneic cell), derived from a subject (e.g., an autologous cell), or from another species (e.g., a xenogeneic cell). In an embodiment, a cell can be grown in cell culture, or prepared from an established cell culture line, or derived from a donor (e.g., a living donor or a cadaver). In an embodiment, a cell is genetically engineered. In another embodiment, a cell is not genetically engineered. A cell may include a stem cell, such as a reprogrammed stem cell, or an induced pluripotent cell. Exemplary cells include mesenchymal stem cells (MSCs), fibroblasts (e.g., primary fibroblasts). HEK cells (e.g., HEK293T), Jurkat cells, HeLa cells, retinal pigment epithelial (RPE) cells, HUVEC cells, NIH3T3 cells, CHO-K1 cells, COS-1 cells, COS-7 cells, PC-3 cells, HCT 116 cells, A549MCF-7 cells, HuH-7 cells, U-2 OS cells, HepG2 cells, Neuro-2a cells, and SF9 cells. In an embodiment, a cell for use in an implantable construct is an RPE cell.

A cell included in an implantable construct may produce or secrete a therapeutic agent. In an embodiment, a cell included in an implantable construct may produce or secrete a single type of therapeutic agent or a plurality of therapeutic agents. In an embodiment, an implantable construct may comprise a cell that is transduced or transfected with a nucleic acid (e.g., a vector) comprising an expression sequence of a therapeutic agent. For example, a cell may be transduced or transfected with a lentivirus. A nucleic acid introduced into a cell (e.g., by transduction or transfection) may be incorporated into a nucleic acid delivery system, such as a plasmid, or may be delivered directly. In an embodiment, a nucleic acid introduced into a cell (e.g., as part of a plasmid) may include a region to enhance expression of the therapeutic agent and/or to direct targeting or secretion, for example, a promoter sequence, an activator sequence, or a cell-signaling peptide, or a cell export peptide. Exemplary promoters include EF-1a, CMV, Ubc, hPGK, VMD2, and CAG. Exemplary activators include the TET1 catalytic domain, P300 core, VPR, rTETR, Cas9 (e.g., from *S. pyogenes* or *S. aureus*), and Cpf1 (e.g., from *L. bacterium*).

An implantable construct described herein may comprise a cell or a plurality of cells. In the case of a plurality of cells, the concentration and total cell number may be varied depending on a number of factors, such as cell type, implantation location, and expected lifetime of the implantable construct. In an embodiment, the total number of cells included in an implantable construct is greater than about 2, 4, 6, 8, 10, 20, 30, 40, 50, 75, 100, 200, 250, 500, 750, 1000, 1500, 2000, 5000, 10000, or more. In an embodiment, the total number of cells included in an implantable construct is greater than about $1.0 \times 10^2$, $1.0 \times 10^3$, $1.0 \times 10^4$, $1.0 \times 10^5$, $1.0 \times 10^6$, $1.0 \times 10^7$, $1.0 \times 10^8$, $1.0 \times 10^9$, $1.0 \times 10^{10}$, or more. In an embodiment, the total number of cells included in an implantable construct is less than about than about 10000, 5000, 2500, 2000, 1500, 1000, 750, 500, 250, 200, 100, 75, 50, 40, 30, 20, 10, 8, 6, 4, 2, or less. In an embodiment, the total number of cells included in an implantable construct is less than about $1.0 \times 10^{10}$, $1.0 \times 10^9$, $1.0 \times 10^8$, $1.0 \times 10^7$, $1.0 \times 10^6$, $1.0 \times 10^5$, $1.0 \times 10^4$, $1.0 \times 10^3$, $1.0 \times 10^2$, or less. In an embodiment, a plurality of cells is present as an aggregate. In an embodiment, a plurality of cells is present as a cell dispersion.

Specific features of a cell contained within an implantable construct may be determined, e.g., prior to and/or after incorporation into the implantable construct. For example, cell viability, cell density, or cell expression level may be assessed. In an embodiment, cell viability, cell density, and cell expression level may be determined using standard techniques, such as cell microscopy, fluorescence microscopy, histology, or biochemical assay.

C. THERAPEUTIC AGENTS

An implantable construct described herein may contain a therapeutic agent, for example, produced or secreted by a cell. A therapeutic agent may include a nucleic acid (e.g., an RNA, a DNA, or an oligonucleotide), a protein (e.g., an antibody, enzyme, cytokine, hormone, receptor), a lipid, a small molecule, a metabolic agent, an oligosaccharide, a peptide, an amino acid, an antigen. In an embodiment, the implantable construct comprises a cell or a plurality of cells that are genetically engineered to produce or secrete a therapeutic agent.

In an embodiment, the implantable construct comprises a cell producing or secreting a protein. The protein may be of any size, e.g., greater than about 100 Da, 200 Da, 250 Da, 500 Da, 750 Da, 1 KDa, 1.5 kDa, 2 kDa, 2.5 kDa, 3 kDa, 4 kDa, 5 kDa, 6 kDa, 7 kDa, 8 kDa, 9 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, 100 kDa, 125 kDa, 150 kDa, 200 kDa, 200 kDa, 250 kDa, 300 kDa, 400 kDa, 500 kDa, 600 kDa, 700 kDa, 800 Da, 900 kDa, or more. In an embodiment, the protein is composed of a single subunit or multiple subunits (e.g., a dimer, trimer, tetramer, etc.). A protein produced or secreted by a cell may be modified, for example, by glycosylation, methylation, or other known natural or synthetic protein modification. A protein may be produced or secreted as a pre-protein or in an inactive form and may require further modification to convert it into an active form.

Proteins produced or secreted by a cell may be include antibodies or antibody fragments, for example, an Fc region or variable region of an antibody. Exemplary antibodies include anti-PD-1, anti-PD-L1, anti-CTLA4, anti-TNFα, and anti-VEGF antibodies. An antibody may be monoclonal or polyclonal. Other exemplary proteins include a lipoprotein, an adhesion protein, blood clotting factor (e.g., Factor VII, Factor VIII, Factor IX, GCG, or VWF), hemoglobin, enzymes, proenkephalin, a growth factor (e.g., EGF, IGF-1, VEGF alpha, HGF, TGF beta, bFGF), or a cytokine.

A protein produced or secreted by a cell may include a hormone. Exemplary hormones include growth hormone, growth hormone releasing hormone, prolactin, lutenizing hormone (LH), anti-diuretic hormone (ADH), oxytocin, thyroid stimulating hormone (TSH), thyrotropin-release hormone (TRH), adrenocorticotropic hormone (ACTH), follicle-stimulating hormone (FSH), thyroxine, calcitonin, parathyroid hormone, aldosterone, cortisol, epinephrine, glucagon, insulin, estrogen, progesterone, and testosterone.

A protein produced or secreted by a cell may include a cytokine. A cytokine may be a pro-inflammatory cytokine or an anti-inflammatory cytokine. Example of cytokines include IL-1, IL-1α, IL-1β, IL-1RA, IL-2, IL-4, IL-5, IL-6, IL-7, IL-8, IL-9, IL-10, IL-11, IL-12, IL-12a, IL-12b, IL-13, IL-14, IL-16, IL-17, G-CSF, GM-CSF, IL-20, IFN-α, IFN-β, IFN-γ, CD154, LT-β, CD70, CD153, CD178, TRAIL, TNF-α, TNF-β, SCF, M-CSF, MSP, 4-1BBL, LIF, OSM, and others. For example, a cytokine may include any cytokine described in M. J. Cameron and D. J. Kelvin, *Cytokines, Chemokines, and Their Receptors* (2013), Landes Biosciences, which is incorporated herein by reference in its entirety.

An implantable construct may comprise a cell expressing a single type of therapeutic agent, e.g., a single protein or nucleic acid, or may express more than one type of therapeutic agent, e.g., a plurality of proteins or nucleic acids. In an embodiment, an implantable construct comprises a cell expressing two types of therapeutic agents (e.g., two types of proteins or nucleic acids). In an embodiment, an implantable construct comprises a cell expressing three types of therapeutic agents (e.g., three types of proteins or nucleic acids). In an embodiment, an implantable construct comprises a cell expressing four types of therapeutic agents (e.g., four types of proteins or nucleic acids).

In an embodiment, an implantable construct comprises a cell expressing a single type of nucleic acid (e.g., DNA or RNA) or may express more than one type of nucleic acid, e.g., a plurality of nucleic acid (e.g., DNA or RNA). In an embodiment, an implantable construct comprises a cell expressing two types of nucleic acids (e.g., DNA or RNA). In an embodiment, an implantable construct comprises a cell expressing three types of nucleic acids (e.g., DNA or RNA). In an embodiment, an implantable construct comprises a cell expressing four types of nucleic acids (e.g., DNA or RNA).

In an embodiment, an implantable construct comprises a cell expressing a single type of protein, or may express more than one type of protein, e.g., a plurality of proteins. In an embodiment, an implantable construct comprises a cell expressing two types of proteins. In an embodiment, an implantable construct comprises a cell expressing three types of proteins. In an embodiment, an implantable construct comprises a cell expressing four types of proteins.

In an embodiment, an implantable construct comprises a cell expressing a single type of enzyme, or may express more than one type of enzyme, e.g., a plurality of enzymes. In an embodiment, an implantable construct comprises a cell expressing two types of enzymes. In an embodiment, an implantable construct comprises a cell expressing three types of enzymes. In an embodiment, an implantable construct comprises a cell expressing four types of enzymes.

In an embodiment, an implantable construct comprises a cell expressing a single type of antibody or antibody fragment or may express more than one type of antibody or antibody fragment, e.g., a plurality of antibodies or antibody fragments. In an embodiment, an implantable construct comprises a cell expressing two types of antibodies or antibody fragments. In an embodiment, an implantable construct comprises a cell expressing three types of antibodies or antibody fragments. In an embodiment, an implantable construct comprises a cell expressing four types of antibodies or antibody fragments.

In an embodiment, an implantable construct comprises a cell expressing a single type of hormone, or may express more than one type of hormone, e.g., a plurality of hormones. In an embodiment, an implantable construct comprises a cell expressing two types of hormones. In an embodiment, an implantable construct comprises a cell expressing three types of hormones. In an embodiment, an implantable construct comprises a cell expressing four types of hormones.

In an embodiment, an implantable construct comprises a cell expressing a single type of enzyme, or may express more than one type of enzyme, e.g., a plurality of enzymes. In an embodiment, an implantable construct comprises a cell expressing two types of enzymes. In an embodiment, an implantable construct comprises a cell expressing three types of enzymes. In an embodiment, an implantable construct comprises a cell expressing four types of enzymes.

In an embodiment, an implantable construct comprises a cell expressing a single type of cytokine or may express more than one type of cytokine, e.g., a plurality of cytokines. In an embodiment, an implantable construct comprises a cell expressing two types of cytokines. In an embodiment, an implantable construct comprises a cell expressing three types of cytokines. In an embodiment, an implantable construct comprises a cell expressing four types of cytokines.

D. FEATURES OF IMPLANTABLE CONSTRUCTS

The implantable construct described herein may take any suitable shape or morphology. For example, an implantable construct may be a sphere, spheroid, tube, cord, string, ellipsoid, disk, cylinder, sheet, torus, cube, stadiumoid, cone, pyramid, triangle, rectangle, square, or rod. An implantable construct may comprise a curved or flat section. In an embodiment, an implantable construct may be prepared through the use of a mold, resulting in a custom shape.

The implantable construct may vary in size, depending, for example, on the use or site of implantation. For example, an implantable construct may have a mean diameter or size greater than 0.1 mm, e.g., greater than 0.25 mm, 0.5 mm, 0.75, 1 mm, 1.5 mm, 2 mm, 3 mm, 4 mm, 5 mm, 6 mm, 7 mm, 8 mm, 9 mm, 10 mm, 20 mm, 30 mm, 40 mm, 50 mm, or more. In an embodiment, an implantable construct may have a section or region with a mean diameter or size greater than 0.1 mm, e.g., greater than 0.25 mm, 0.5 mm, 0.75, 1 mm, 1.5 mm, 2 mm, 3 mm, 4 mm, 5 mm, 6 mm, 7 mm, 8 mm, 9 mm, 10 mm, 20 mm, 30 mm, 40 mm, 50 mm, or more. In an embodiment, an implantable construct may have a mean diameter or size less than 1 cm, e.g., less 50 mm, 40 mm, 30 mm, 20 mm, 10 mm, 7.5 mm, 5 mm, 2.5 mm, 1 mm, 0.5 mm, or smaller. In an embodiment, an implantable construct may have a section or region with a mean diameter or size less than 1 cm, e.g., less 50 mm, 40 mm, 30 mm, 20 mm, 10 mm, 7.5 mm, 5 mm, 2.5 mm, 1 mm, 0.5 mm, or smaller.

An implantable construct comprises at least one zone capable of preventing exposure of an enclosed antigenic or therapeutic agent from the outside milieu, e.g., a host effector cell or tissue. In an embodiment, the implantable construct comprises an inner zone (IZ). In an embodiment, the implantable construct comprises an outer zone (OZ). In an embodiment, either the inner zone (IZ) or outer zone (OZ) may be erodible or degradable. In an embodiment, the inner zone (IZ) is erodible or degradable. In an embodiment, the outer zone (OZ) is erodible or degradable. In an embodiment, the implantable construct comprises both an inner zone (IZ) and an outer zone (OZ), either of which may be erodible or degradable. In an embodiment, the implantable construct comprises both an inner zone (IZ) and an outer zone (OZ), wherein the outer zone is erodible or degradable. In an embodiment, the implantable construct comprises both an inner zone (IZ) and an outer zone (OZ), wherein the inner zone is erodible or degradable. The thickness of either of the zone, e.g., either the inner zone or outer zone, may be correlated with the length or duration of a "shielded" phase, in which the encapsulated antigenic or therapeutic agent is protected or shielded from the outside milieu, e.g., a host effector cell or tissue.

The zone (e.g., the inner zone or outer zone) of the implantable construct may comprise a degradable entity, e.g., an entity capable of degradation. A degradable entity may comprise an enzyme cleavage site, a photolabile site, a pH-sensitive site, or other labile region that can be eroded or comprised over time. In an embodiment, the degradable entity is preferentially degraded upon exposure to a first condition (e.g., exposure to a first milieu, e.g., a first pH or first enzyme) relative to a second condition (e.g., exposure to a second milieu, e.g., a second pH or second enzyme). In one embodiment, the degradable entity is degraded at least 2, 5, 10, 20, 30, 40, 50, 60, 70, 80, or 100 times faster upon exposure to a first condition relative to a second condition. In an embodiment, the degradable entity is an enzyme cleavage site, e.g., a proteolytic site. In an embodiment, the degradable entity is a polymer (e.g., a synthetic polymer or a naturally occurring polymer, e.g., a peptide or polysaccharide). In an embodiment, the degradable entity is a substrate for an endogenous host component, e.g., a degradative enzyme, e.g., a remodeling enzyme, e.g., a collagenase or metalloprotease. In an embodiment, the degradable entity comprises a cleavable linker or cleavable segment embedded in a polymer.

In an embodiment, an implantable construct comprises a pore or opening to permit passage of an object, such as a small molecule (e.g., nutrients or waste), a protein, or a nucleic acid. For example, a pore in or on an implantable construct may be greater than 0.1 nm and less than 10 μm.

In an embodiment, the implantable construct comprises a pore or opening with a size range of 0.1 μm to 10 μm, 0.1 μm to 9 μm, 0.1 μm to 8 μm, 0.1 μm to 7 μm, 0.1 μm to 6 μm, 0.1 μm to 5 μm, 0.1 μm to 4 μm, 0.1 μm to 3 μm, 0.1 μm to 2 μm.

An implantable construct described herein may comprise a chemical modification in or on any enclosed material. Exemplary chemical modifications include small molecules, peptides, proteins, nucleic acids, lipids, or oligosaccharides. The implantable construct may comprise at least 0.5%, 1%, 2%, 3%, 4%, 5%, 7.5%, 10%, 15%, 20%, 30%, 40%, 50%, 60%, 70%, 80% or more of a material that is chemically modified, e.g., with a chemical modification described herein. An implantable construct may be partially coated with a chemical modification, e.g., at least about 5%, 10%, 15%, 20%, 25%, 30%, 35%, 40%, 45%, 50%, 55%, 60%, 65%, 70%, 75%, 80%, 85%, 90%, 95%, 99%, or 99.9% coated with a chemical modification.

In an embodiment, the implantable construct is formulated such that the duration of release of the antigenic and/or therapeutic agent is tunable. For example, an implantable construct may be configured in a certain manner to release a specific amount of an antigenic or therapeutic agent over time, e.g., in a sustained or controlled manner. In an embodiment, the implantable construct comprises a zone (e.g., an inner zone or an outer zone) that is degradable, and this controls the duration of therapeutic release from the construct by gradually ceasing immunoprotection of encapsulated cells or causing gradual release of the antigenic agent. In an embodiment, the implantable construct is configured such that the level of release of an antigenic or therapeutic agent is sufficient to modulate the ratio of a host effector cell, e.g., a host T cell. In an embodiment, the implantable construct is configured such that the level of release of an antigenic or therapeutic agent is sufficient to activate a host cell (e.g., a host T effector cell or a host NK cell) or increase the level of certain host cells (e.g., host T effector cells or host NK cells). In an embodiment, the implantable construct is configured such that the level of release of an antigenic or therapeutic agent is not sufficient to activate a host regulator cell (e.g., a host T regulator cell) or increase the level of host regulator cells (e.g., host T regulator cells).

In some embodiments, the implantable construct comprises a zone that is targeted by the natural foreign body response (FBR) of a host or subject, e.g., over a period of time. In an embodiment, the implantable construct is coated with fibrotic overgrowth upon administration to a subject, e.g., over a period of time. Fibrotic overgrowth on the surface of the implantable construct may lead to a decrease in function of the implantable construct. For example, a decrease in function may comprise a reduction in the release of an antigenic or therapeutic agent over time, a decrease in pore size, or a decrease in the diffusion rate of oxygen and other key nutrients to the encapsulated cells, leading to cell death. In an embodiment, the rate of fibrotic overgrowth may be tuned to design a dosing regimen. For example, the fibrotic overgrowth on the surface of an implantable construct may result in a decrease in function of the implantable construct about 6 hours, 12 hours, 18 hours, 1 day, 2 days, 3 days, 4 days, 5 days, 6 days, 7 days, 8 days, 9 days, 10 days, 11 days, 12 days, 13 days, 2 weeks, 2.5 weeks, 3 weeks, 4 weeks, or 6 weeks after administration (e.g., injection or implantation) to a subject.

In some embodiments, the implantable construct is chemically modified with a specific density of modifications. The specific density of chemical modifications may be described as the average number of attached chemical modifications per given area. For example, the density of a chemical modification on or in an implantable construct may be 0.01, 0.1, 0.5, 1, 5, 10, 15, 20, 50, 75, 100, 200, 400, 500, 750, 1,000, 2,500, or 5,000 chemical modifications per square um or square mm.

An implantable construct may be formulated or configured for implantation in any organ, tissue, cell, or part of a subject. For example, the implantable construct may be implanted or disposed into the intraperitoneal space of a subject. An implantable construct may be implanted in or disposed on a tumor or other growth in a subject, or be implanted in or disposed about 0.1 mm, 0.5 mm, 1 mm, 0.25 mm, 0.5 mm, 0.75, 1 mm, 1.5 mm, 2 mm, 3 mm, 4 mm, 5 mm, 6 mm, 7 mm, 8 mm, 9 mm, 10 mm, 20 mm, 30 mm, 40 mm, 50 mm, 1 cm, 5, cm, 10 cm, or further from a tumor or other growth in a subject. An implantable construct may be configured for implantation, or implanted, or disposed on or in the skin, a mucosal surface, a body cavity, the central nervous system (e.g., the brain or spinal cord), an organ (e.g., the heart, eye, liver, kidney, spleen, lung, ovary, breast, uterus), the lymphatic system, vasculature, oral cavity, nasal cavity, gastrointestinal tract, bone, muscle, adipose tissue, skin, or other area.

An implantable construct may be formulated for use for any period of time. For example, an implantable construct may be used for 1 hour, 2 hours, 4 hours, 6 hours, 12 hours, 1 day, 36 hours, 2 days, 3 days, 4 days, 5 days, 6 days, 1 week, 2 weeks, 3 weeks, 4 weeks, 5 weeks, 6 weeks, 2 months, 3 months, 4 months, 5 months, 6 months, 1 year, or longer. An implantable construct can be configured for limited exposure (e.g., less than 2 days, e.g., less than 2 days, 1 day, 24 hours, 20 hours, 16 hours, 12 hours, 10 hours, 8 hours, 6 hours, 5 hours, 4 hours, 3 hours, 2 hours, 1 hour or less). A implantable construct can be configured for prolonged exposure (e.g., at least 2 days, 3 days, 4 days, 5 days, 6 days, 7 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more). An implantable construct can be configured for permanent exposure (e.g., at least 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more).

E. METHODS OF TREATMENT

Described herein are implantable constructs comprising a zone (e.g., a layer) encapsulating an antigenic or therapeutic agent, and related methods of use thereof. In an embodiment, the implantable constructs are used to treat a disease, e.g., as described herein.

In some embodiments, the disease is a proliferative disease. In an embodiment, the proliferative disease is cancer. A cancer may be an epithelial, mesenchymal, or hematological malignancy. A cancer includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). In an embodiment, the cancer is a solid tumor (e.g., carcinoid, carcinoma or sarcoma), a soft tissue tumor (e.g., a heme malignancy), or a metastatic lesion, e.g., a metastatic lesion of any of the cancers disclosed herein. In an embodiment, the cancer is a fibrotic or desmoplastic solid tumor.

Exemplary cancers include carcinoma, lymphoma, blastoma, sarcoma, and leukemia or lymphoid malignancies. In an embodiment, the cancer affects a system of the body, e.g., the nervous system (e.g., peripheral nervous system (PNS) or central nervous system (CNS)), vascular system, skeletal system, respiratory system, endocrine system, lymph system, reproductive system, or gastrointestinal tract. In some embodiments, cancer affects a part of the body, e.g., blood, eye, brain, skin, lung, stomach, mouth, ear, leg, foot, hand, liver, heart, kidney, bone, pancreas, spleen, large intestine, small intestine, spinal cord, muscle, ovary, uterus, vagina, or penis. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Other examples of cancers include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

In an embodiment, the implantable construct is used to treat a neurodegenerative disease, autoimmune disease (e.g., diabetes, multiple sclerosis, lupus, occlusions, capsular contractions), or a liver disease (e.g., hepatitis B infection, hepatitis C infection, cirrhosis, or liver cancer) in a subject. In some embodiments, the disease is diabetes (e.g., type 1 diabetes or type 2 diabetes). In some embodiments, the condition is fibrosis. In some embodiments, the condition is inflammation.

The implantable construct described herein may be used in a method to modulate (e.g., upregulate) the immune response in a subject. For example, upon administration to a subject, the implantable construct (or an antigenic and/or therapeutic agent disposed within) may modulate (e.g., upregulate) the level of a component of the immune system in a subject (e.g., increasing the level or decreasing the level of an immune system component). Exemplary immune system components that may be modulated by an implantable construct or related method described herein include stem cells (hematopoietic stem cells), NK cells, T cells (e.g., an adaptive T cell (e.g., a helper T cell, a cytotoxic T cell, memory T cell, or regulatory T cell) or an innate-like T cell (e.g., natural killer T cell, mucosal-associated invariant T cell, or gamma delta T cell), B cells, an antibody or fragment thereof, or other another component. In an embodiment, the modulation comprises increasing or decreasing the activation of a T cell or other immune system component (e.g., by about 5%, 10%, 15%, 20%, 25%, 30%, 35%, 40%, 45%, 50%, 55%, 60%, 65%. 70%, 75%, 80%, 85%, 90%, 95%, 99%, or more compared with a control).

The implantable construct described herein may be used to modulate the immune response in a subject for a specific period of time. For example, administration of the implantable construct (or an antigenic and/or therapeutic agent disposed within) may activate the immune response (e.g., by increase in the level of an immune system component) in a subject for at least 1 hour, 2 hours, 3 hours, 4 hours, 6 hours, 8 hours, 10 hours, 12 hours, 16 hours, 20 hours, 1 day, 1.5 days, 2 days, 3 days, 4 days, 5 days, 6 days, 1 week, 1.5 weeks, 2 weeks, 3 weeks, 4 weeks, 5 weeks, 6 weeks, 2 months, 2.5 months, 3 months, 4 months, 5 months, 6 months, or longer. In an embodiment, administration of the implantable construct activates the immune response (e.g., by increase in the level of an immune system component) in a subject between 1 hour and 1 month, 1 hour and 3 weeks, 1 hour and 2 weeks, 1 hour and 1 week, 6 hours and 1 week, or 6 hours and 3 days. In an embodiment, implantation of the implantable construct (e.g., an implantable construct described herein) results in upregulation of T cells in a subject, e.g., as measured by a blood test, for at least 1 day.

The implantable constructs described herein may further comprise an additional pharmaceutical agent, such as an anti-proliferative agent, anti-cancer agent, anti-inflammatory agent, an immunomodulatory agent, or a pain-relieving agent, e.g., for use in combination therapy. The additional pharmaceutical agent may be disposed in or on the implantable construct or may be produced by a cell disposed in or on the implantable construct. In an embodiment, the additional pharmaceutical agent is small molecule, a protein, a peptide, a nucleic acid, an oligosaccharide, or other agent.

In an embodiment, the additional pharmaceutical agent is an anti-cancer agent. In some embodiments, the anti-cancer agent is a small molecule, a kinase inhibitor, an alkylating agent, a vascular disrupting agent, a microtubule targeting agent, a mitotic inhibitor, a topoisomerase inhibitor, an anti-angiogenic agent, or an anti-metabolite. In an embodiment, the anti-cancer agent is a taxane (e.g., paclitaxel, docetaxel, larotaxel or cabazitaxel). In an embodiment, the anti-cancer agent is an anthracycline (e.g., doxorubicin). In some embodiments, the anti-cancer agent is a platinum-based agent (e.g., cisplatin or oxaliplatin). In some embodiments, the anti-cancer agent is a pyrimidine analog (e.g., gemcitabine). In some embodiments, the anti-cancer agent is chosen from camptothecin, irinotecan, rapamycin, FK506, 5-FU, leucovorin, or a combination thereof. In other embodiments, the anti-cancer agent is a protein biologic (e.g., an antibody molecule), or a nucleic acid therapy (e.g., an antisense or inhibitory double stranded RNA molecule).

In an embodiment, the additional pharmaceutical agent is an immunomodulatory agent, e.g., one or more of an activator of a costimulatory molecule, an inhibitor of an immune checkpoint molecule, or an anti-inflammatory agent. In an embodiment, the immunomodulatory agent is an inhibitor of an immune checkpoint molecule (e.g., an inhibitor of PD-1, PD-L1, LAG-3, TIM-3 or CTLA4, or any combination thereof). In some embodiments, the immunomodulatory agent is a cancer vaccine.

In some embodiments, the immunomodulatory agent is an inhibitor of PD-1, PD-L1, PD-L2, CTLA4, TIM3, LAG3, VISTA, BTLA, TIGIT, LAIR1, CD73, CD160, 2B4 and/or TGFR beta. In one embodiment, the inhibitor of an immune checkpoint molecule inhibits PD-1, PD-L1, LAG-3, TIM-3 or CTLA4, or any combination thereof. Inhibition of an inhibitory molecule can be performed at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof that binds to PD-1, PD-L1, PD-L2, CTLA4, TIM3, LAG3, VISTA, BTLA, TIGIT, LAIR1, CD73, CD160, 2B4 and/or TGFR beta, or a combination thereof. In some embodiments, the immunomodulatory agent is an anti-inflammatory agent, e.g., an anti-inflammatory agent as described herein. In an embodiment, the anti-inflammatory agent is an agent that blocks, inhibits, or reduces inflammation or signaling from an inflammatory signaling pathway. In an embodiment, the anti-inflammatory agent inhibits or reduces the activity of one or more of any of the following an immune component of the subject. In an embodiment, the anti-inflammatory agent is an IL-1 or IL-1 receptor antagonist, such as anakinra, rilonacept, or canakinumab. In an embodiment, the anti-inflammatory agent is an IL-6 or IL-6 receptor antagonist, e.g., an anti-IL-6 antibody or an anti-IL-6 receptor antibody, such as tocilizumab (ACTEMRA®), olokizumab, clazakizumab, sarilumab, sirukumab, siltuximab, or ALX-0061. In an embodiment, the anti-inflammatory agent is a TNF-α antagonist, e.g., an anti-TNF-α antibody, such as infliximab (REMICADE®), golimumab (SIMPONI®), adalimumab (HUMIRA®), certolizumab pegol (CIMZIA®) or etanercept. In one embodiment, the anti-inflammatory agent is a corticosteroid, e.g., as described herein.

F. COMPOSITIONS AND ADMINISTRATIONS OF IMPLANTABLE CONSTRUCTS

The present disclosure features pharmaceutical compositions comprising an implantable construct comprising a zone (e.g., an inner zone and optionally an outer zone, both of which may be degradable), and an antigenic and/or therapeutic agent, and optionally a pharmaceutically acceptable excipient. In some embodiments, the implantable construct is provided in an effective amount in the pharmaceutical composition. In some embodiments, the effective amount is a therapeutically effective amount. In some embodiments, the effective amount is a prophylactically effective amount.

Pharmaceutical compositions described herein can be prepared by any method known in the art of pharmacology. In general, such preparatory methods include the steps of bringing the implantable construct into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the implantable construct may be generally equal to the dosage of the antigenic and/or therapeutic agent which would be administered to a subject and/or a convenient fraction of such a dosage such as, for example, one-half or one-third of such a dosage.

Relative amounts of the implantable construct, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of any component.

The implantable construct and a pharmaceutical composition thereof may be administered or implanted orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally. In an embodiment, the implantable construct is injected subcutaneously. In an embodiment, the implantable construct is injected into the intraperitoneal space. In an embodiment, the implantable construct is injected into the intraperitoneal space. In an embodiment, the implantable constructed is delivered to the subject using a device, e.g., a cannula or catheter.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For ophthalmic use, provided compounds, compositions, and devices may be formulated as micronized suspensions or in an ointment such as petrolatum.

In an embodiment, the release of an antigenic, therapeutic, or additional pharmaceutical agent is released in a sustained fashion. In order to prolong the effect of a particular agent, it is often desirable to slow the absorption of the agent from injection. This can be accomplished by the use of a liquid suspension of crystalline or amorphous material with poor water solubility. The rate of absorption of the agent then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The implantable constructs provided herein are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific therapeutic agent employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

An effective amount of a therapeutic agent released from the implantable construct may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of therapeutic agent per unit dosage form (e.g, per implantable construct).

The therapeutic agent administered may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

G. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Cell Engineering and Cell Culture

Reagents. Cell culture media and associated reagents, such as transfection media, were purchased through Fisher Scientific. Lipofection reagents (Lipofectamine 3000®) and selection media (puromycin) were purchased from Invitrogen. Expression vectors and helper plasmids were developed and subsequently purchased from VectorBuilder. CellTiter-Glo® was purchased from Promega. TrypanBlue® and Live Dead® stains were purchased from Fisher Scientific. Alginate compounds were purchased from PRONOVA. The encapsulation apparatus used contains syringe pumps from Harvard Apparatus and co-axial nozzles from Ramé-Hart. All animals were purchased from Jackson Labs. Alginate compounds were purchased through PRONOVA.

Cell Culture. ID8/MOSEC cells were obtained commercially from EMD Millipore, Sigma. PAN02 or PANC02 mouse cells were obtained from The Division of Cancer Treatment and Diagnosis (DCTD), National Cancer Institute. Human ARPE-19 cells were obtained from ATCC. ARPE-19 cells were cultured using Dulbecco's Modified Eagle Medium (DMEM/F-12), with 10% non-heat inactivated Fetal Bovine Serum (FBS) and 1% antibiotic-antimycotic (AA). When cells reached 70-90% confluency, the culture medium was discarded, and cells were briefly washed with 5 mL of DPBS. Washing solution was aspirated and followed by 5 ml TrypLE to disperse the cell layer. Cells were incubated for 3 minutes, then observed under a microscope to ensure detachment. 7 ml of complete growth medium were added to the flask to stop the TrypLE reaction. The cell suspension was transferred to a 15 ml confocal tube and centrifuged for 5 minutes at 250×g. The supernatant was aspirated, and the pellet resuspended in 1 ml of complete media and redistributed in sterile T-75 flasks at the desired concentration. 13 ml complete media were added to the flask and cells were incubated at 37° C. in a 5% CO2 humidified atmosphere. Media used for B16-F10 was DME/F-12, 10% FBS, 1% antibiotic-antimycotic (AA). Media used for ID8 was DMEM High Glucose, 4% FBS, 1% AA, and 1% ITS. The media was changed 3 times weekly. Cells were passaged four times before use in transfection. Pan02, and ID8 cells were cultured using the same methods.

Plasmids for lentiviral transduction and lipofectamine transfections of all cells used were designed and purchased from VectorBuilder in DNA MaxiPrep form. ARPE-19 cells were engineered to express mouse IL2 and firefly luciferase. ID8/MOSEC cells were engineered to express firefly luciferase. Engineered cells were assayed for linearity between luciferase expression and cell number using IVIS imaging. ARPE cytokine expressing cell lines were assayed for cell viability and changes in doubling time post-transfection/transduction using traditional cell subculture methods and trypan blue based counting methods.

Cell Transfection/Lipofection. For transfection of native mouse IL-2, cells that had been passaged four times were seeded into 6 well plates at a concentration of 400,000 cells per well, with 3 mL complete media. The plate was incubated overnight at 37° C. in a 5% CO2 humidified atmosphere. 24 hours following seeding, the culture medium was aspirated, and each well was primed with 2 mL Opti-MEM serum free medium. In an Eppendorf tube a 2:1 ratio of expression vector to helper plasmid was added to 125 μl of Opti-MEM, with 6 μl P3000. This solution was incubated at room temperature for 5 minutes. In a new Eppendorf tube 125 µl Opti-MEM was mixed with 3.75 µl of lipofectamine3000. Values were adjusted based on the number of wells. The Eppendorf tubes containing lipofectamine3000 were combined with the DNA complex and incubated at room temperature for 15 minutes. Opti-MEM used to prime the wells was discarded, and 2.5 mL fresh Opti-MEM was added to each well. The DNA-lipid complexes were then added (250 µl per well) to five of six wells with the last well remaining as a control. After incubation at 37° C. for 4 hours, the transfection media was replaced with fresh culture media containing 10% FBS and 1% streptomycin antibiotic. Four days after transfection, culture medium was aspirated, and cells were transferred to a T-75 flask, with 15 mL of DMEM with 10% FBS, 1% SP, and 50 µl/500 ml puromycin. On the fourth day, cells were selected for expression with puromycin for one week and then maintain using normal cell culture techniques. This procedure was used for transfection of each of the following cytokines; IL2, IL7, IL10, IL12, and IL15.

Cell Viability/Doubling Time Analysis. ARPE-19 cells were engineered to express various proteins, such as mouse IL2, mouse IL7, mouse IL12, mouse IL15, firefly luciferase, and metridia luciferase. PAN02 and ID8/MOSEC cells were engineered to express firefly luciferase. The sequences of each of these proteins is provided in Table 1. PAN02, ID8/MOSEC, ARPE-19 f-Luc & met-Luc cells were assayed for linearity between luciferase expression and cell number using IVIS imaging (methods followed small animal imaging described below.) Engineered ARPE cells were assayed for cell viability and changes in doubling time post-transfection/transduction using traditional cell subculture methods and trypan blue based counting methods.

Cell Transduction. Cells were transduced using a standard $3^{rd}$ generation lentivirus protocol. Lentivirus was produced by transfection of 3 packaging plasmids (pMLg/PRRE, pRSV-Rev and pMD2.g) together with an expression vector in HEK293T cells. 6-8 hours after transfection, the cell media was replaced with new media and cells were cultured for 36-48 hours. The lentivirus was concentrated and used with polybrene to transduce Pan02 or ID8/MOSEC cells which had been plated the day before and were at 70-80% confluency. After a 24-hour incubation with the virus, the media was changed, and the cells were cultured for 3 days. On the fourth day, cells were selected for expression with puromycin for one week and then maintain using normal cell culture techniques.

Example 2: Quantification of Production by ELISA

Cells from each group were grown up into a T-150 flask in DMEM media with 10% FBS, 1% Penstrep, and 0.5 µl/500 ml puromycin. At confluency, culture media was aspirated and 10 ml TrypLE was added. Cells were incubated for 3 minutes at 37° C. in a 5% $CO_2$ humidified atmosphere. Once the cell layer was dispersed, 10 ml's complete media was added to stop the reaction. The cell suspension was transferred to a 50 ml conical tube and centrifuged at 250G for 5 minutes. The supernatant was aspirated, and cells were re-suspended in 1 ml complete media. Cell concentration was counted using a Countess™ hemocytometer. The volume required to achieve a concentration of 10,000 cells in 200 µl was calculated based on the concentration of live cells in the sample. Of the remaining cell suspension volume, 1 million cells were resuspended in 1 ml alginate to be synthesized into core shell capsules. All groups were incubated for 24 hours at 37° C. in a 5% $CO_2$ humidified atmosphere. Cell supernatant was collected from each well and transferred to a 2 ml microfuge tube at the 24-hour time period. All samples were centrifuged at 1000G for 20 minutes. After centrifuging the samples, media was transferred from each 2 ml tube into a 96 well plate; again. Samples were diluted 1:2 in complete media for a total volume of 400 µl. Mouse IL7 Quantikine ELISA Kit (CAT M7000), Human IL7 ELISA Kit (CAT AB185984), M IL15 ELISA Kit (CAT RAB0206-1KT), Human IL15 ELISA Kit (CAT AB218266), LEGEND MAX Human IL10 ELISA kit, ELISA MAX Deluxe set Mouse IL10 (CAT 431414), (CAT 430608), LEGEND MAX Mouse IL2 ELISA Kit (CAT 431007), LEGEND MAX Human IL2 ELISA Kit (CAT 431808) The assay was run according to protocols provided by the company. All samples were run in triplicate.

Example 3: T Cell Proliferation Assay

A EasySep T Cell Isolation Kit (StemCell Technologies) and associated reagents and devices were used to isolate T cell from C57BL6 mouse spleens (Jackson Labs). Cells were plated in 96 well plates at 10,000 cells/well in 100 ul RPMI 1640. Cells were supplemented with 0.1, 1, 5 or 10 ng/mL of cell produced native IL2 or 1 or 10 ng/mL of recombinant IL-2 (Miltenyi). 24 or 72 hours after incubation at 37 C, cell proliferation (and viability) was measured using CellTiter-Glo Luminescent Cell Viability Assay (Promega).

Example 4: Encapsulation of Cells

Alginate hydrogel spheres were synthesized using a custom-built, two-fluid co-axial electrostatic spraying device. The device consisted of a voltage generator that was attached to the tip of a co-axial needle and grounded to a 1:4 barium chloride: mannitol crosslinking bath. The co-axial needle was fed by two separate syringes containing 1.4% alginate solutions that were diluted in 0.9% saline. In order to suspend cells in alginate, cells that had reached 70-90% confluency were removed of supernatant and washed with 5 ml's of DPBS. The washing solution was aspirated and followed by 5 ml's TrypLE to disperse the cell layer. Cells were incubated for 3 minutes, then observed under a microscope to ensure detachment. 7 mL's of complete growth medium was added to the flask to stop the TrypLE reaction. The cell suspension was transferred to a 50 ml conical tube and centrifuged for 5 minutes at 250G. The supernatant was aspirated, and the palette was broken. The desired volume of SLG20 alginate was added to the cells and pulled up by a 5 ml Luer lock syringe. Syringes containing the two different alginates (SLG20, and RZA15-modifed alginate) were placed in two separate syringe pumps that were fed into a co-axial nozzle which was then suspended over 150 ml of the crosslinking bath; RZA15 alginate fed into the horizontal axis of the nozzle which made the shell, while SLG20 fed into the vertical axis of the nozzle which made the core. Flow rates for each syringe were adjusted to a ratio of 5 ml/hr. Size of the capsules was maintained by adjusting the voltage on the generator; a voltage of ~5.30 most consistently produced capsules that were 1.5 mm in diameter. Capsules were decanted in order to separate them from the crosslinking bath. They were subsequently washed 3 times with HEPES buffer, and 3 times with complete cell medium. Finally, encapsulated cells were transferred to a T-25 flask containing 6 mls of complete media and maintained as plated cells would be; media changes every 2-3 days. Following encapsulation, cells were washed with 5 ml DPBS and stained using a stock 1.25 µl of ~2 µM calcein AM and 20 µl of 4 µM EthD-1 in DPBS. The sample was incubated for 20 minutes and imaged using a fluorescence microscope. Twenty capsules were imaged from each sample group of encapsulated cells and examined for live and dead cells; a GFP filter was used to capture live cells and a Texas Red filter was used to capture dead cells.

Example 5: Tumor Implantation Protocols

Implantable constructs were investigated for their effects in vivo following the protocol described below.

Tumor Implants. The following mouse tumor models were prepared for implantation: (melanoma, Pan02, and ID8), and tracking of tumor size was carried out in vivo. C57BL6/J black mice were used for all in vivo tumor regression studies. To perform these studies, C57BL6/J black male and female mice (6-8 weeks old and each weighing ~18-25 gm) were procured from Jackson Laboratories. All animal studies were performed based on the approval by IACUC approval.

Tumor Injection. For subcutaneous model of melanoma and Pan02, C57BL6/J mice were subcutaneously injected with 1 million cells (B16F10 or Pan02). The cells were suspended in saline and injected using an insulin syringe. For, IP tumor model for ID8 and Pan02, $5^6$ cells (suspended in saline) were intraperitoneally injected to the lower right abdomen of the C57BL6/J mice.

Subcutaneous Tumors. For SubQ melanoma and pancreatic tumor model melanoma, the tumor volume was measured by using the formula (0.5×ab 2), where 'a' represents the longest dimension and 'b' represents the shortest dimension of the tumors. Also, the weight and picture of the tumors were taken after the sacrifice.

Intraperitoneal Tumors. Animals injected with PAN02 or ID8 cancer cell lines were tracked every other day for 7-10 days before they were selected for implantation surgery, sham surgeries, or untreated control groups. After surgery, animals were tracked for tumor growth or reduction using small animal IVIS imaging (methods described below).

Animal Surgeries. Anesthesia & Analgesia: All procedures were conducted under anesthesia and treated with subsequent analgesia. Mice used in studies were anesthetized with isoflurane (1-4%) and oxygen (1-2 L) using a rodent anesthesia machine by tank induction followed by nose cone maintenance. Pedal withdrawal reflex was used to evaluate the depth of anesthesia for gas anesthesia before beginning any invasive procedure and respiration was monitored continuously to ensure sufficient anesthesia. Body temperatures were regulated during anesthesia and recovery through the use of water circulating heating pads. Importantly, the depth of anesthesia was continuously monitored throughout the surgeries.

Surgeon: Surgeons were required to wear a surgical mask and a clean lab coat. Sterile surgeon's gloves were used. When donning the sterile gloves, care was taken to prevent contamination of the outer sterile surface of the glove. Once gloved, care was taken to only touch the sterile operative field and equipment. Additional surgeon preparation precautions such as cap and sterile gown were employed when there were surgical cases with increased risk for clinical infection.

Intraperitoneal (IP) surgical implantation of capsules Animals were all weighed, ear punch identified, and shaved along their abdomen prior to surgery as part of their preoperative care. This was followed by one scrub with isopropyl alcohol followed by a second scrub with Betadine Surgical Scrub (7.5% povidone-iodine; Patterson Vet). These anti-septic scrubbing steps were repeated three times.

A sharp surgical blade (15T; Sklar) was then used to cut a 0.5-0.75 cm midline incision through the skin and the linea alba into the abdomen. The surgeon kept the incision as small as possible with 0.75 cm being the largest possible incision size. Capsule implants were introduced into the peritoneal cavity. The abdominal muscle was closed by suturing with 5-0 Ethicon black PDS-absorbable or other 5.0-6.0 monofilament absorbable sutures. The external skin layer was closed with PDS suture as previously described. Blood and tissue debris were removed from the surgical instruments between procedures with sterile water or saline and the instruments were resterilized between animals (maximum of 5 procedures) using a hot bead sterilizer. After the surgery, the animals were put back in the cage to recover on a heating pad and monitored until ambulating.

Post-Operative Care: Food was placed on the bottom of the cage for 48 hrs post-op to limit rearing and possible muscle suture rupture or hernias from recovering animals Animals were monitored daily for four days post op for weight, general grooming, socialness, signs of dehiscence, dehydration, infection or blood loss from the suture site or in the stool. If suture sites were found open with no organ prolapse or significant bleeding the animals were anesthetized (1-4% isoflurane, 1-2 L/min O2) in an induction tank and transferred to a nose cone for wound closure using wound glue (VetBond 3M, Patterson Vet).

Humane Endpoints & Euthanasia. if any adverse events were encountered during surgery animals were euthanized by anesthesia with 1-4% isoflurane & 1-2 L/min $O_2$ followed by 2 L/min $CO_2$ until signs of respiration were no longer evident. At this point, animals were cervically dislocated to ensure death. In the postoperative period if humane endpoints were identified (lack of grooming, toe walking, hunched posture, social isolation, piloerected fur, severe dehiscence, significant blood loss) animals were euthanized. All euthanasia is in accordance with the approved IACUC protocol approved at Rice University and in accordance with the AVMA Guidelines for the Euthanasia of Animals.

Example 6: Quantification of Tumor Regression Studies

FACS. Antibody cocktails: Anti-mouse CD19, CD25, CD44, CD161, CD62L, CD4, FoxP3, CD3e, CD8, PD-1, Ly6G, F4/80, CD11b, CD11c, and CD45 were commercially obtained and resuspended in Perm/Wash buffers at vendor recommended dilutions (1:50, 1:100, 1:200, 1:400) per each antibody. All antibody cocktails were prepared the day of staining and maintained in the dark at 4° C. or in ice.

Sample Collection & Animal Handling. Animals were anesthetized in isoflurane (1-4%, 1.5 O2 L/min) in an induction chamber and transferred to a nose cone. After checking pedal reflexes, cardiac puncture was performed and blood collected and maintained in 0.5M EDTA coated tubes stored at 4° C. for downstream processing Animals were then cervically dislocated as a secondary method to ensure death. Animals were then cut along their midline through both skin and muscle layers, 10 mL's of 0.2 micron filtered sterile saline are then flushed through the intraperitoneal space to collect IP fluids and cells. IP fluids were maintained at 4° C. or in ice thereafter. Spleens and livers are then immediately harvested. Spleens were stored on ice for downstream processing and livers placed into histology cassettes (ThermoFisher) and fixed immediately in formalin and maintained at room temperature (10% v/v, Thermo Scientific, Richard-Allen Scientific). All animal handling procedures are in accordance with approved IACUC protocols at Rice University and are conducted at Rice University.

Sample Processing. all samples are maintained on ice or kept at 4° C. throughout the processing and staining procedures below.

Spleens: Spleens were mashed using pestles against a strainer. Spleen tissue samples were then washed three times using RPMI media (Gibco), spun down (2000 rpm, 3 min, RT) then resuspended in 3 mL of RBC lysis buffer (Sigma) and incubated for 10 min at room temperature. After incubation 10 mL of RPMI media was added to the spleen solution, the sample was mixed then spun down (2000 rpm, 3 min, RT) then resuspended in FACS buffer (PBS, 2% calf serum, 1 mM EDTA, 0.1% Sodium Azide) and counted for cell concentration using Trypan Blue (ThermoFisher).

IP Fluid: Collected IP fluid (10 ml) was filtered through a 70-micron strainer, spun down (2000 rpm, 3 min, RT) then resuspended in 3 ml of RBC Lysis Buffer and left to incubate for 10 min at room temperature.

Blood Samples: RBC lysis buffer (2 parts) was added to the blood sample (1 part) and then vortexed. The sample was allowed to incubate for 3 min at room temperature. The sample was then spun down (15,000 rpm, 5 min, RT) then resuspended in 300 uL of FACS buffer, this wash step was repeated one more time followed by a final filtration step through a 70-micron strainer.

Sample Staining. Samples were plated into deep 96 well plates at a density of approximately 2.5 million cells/well. Plates are spun down (500 g, 5 min, RT) and resuspended in FACS buffer.

Extracellular Staining: plates were spun down (500 g, 5 min, RT) and resuspended in 50 μl of Fc block buffer (0.25 μg of CD16/CD32 added per one million cells into 50 μl of FACS buffer). Plates were then left to incubate for 10 min on ice in the dark. 150 μl of cold FACS buffer was added and mixed with the suspension of Fc block solution. Samples were then split in half and aliquoted to a second deep 96-well plate. 100 μl of cold FACS buffer was added to each well for both deep 96 well plates followed by a centrifuge step (400 g, 5 min, 4° C.). Supernatants were removed from both plates and the pellets were resuspended in 50 μl of antibody cocktails. Samples were then allowed to stain for 30 min, at 4 C in the dark. Plates were then spun down (500 g, 5 min, 4° C.) and resuspended in 100 μl of cold FACS buffer, this wash step was repeated once more.

Intracellular Staining: intracellular staining occurred immediately following extracellular staining. Cell pellets in both plates were resuspended in 200 μl of a Fixation/Permeabilization solution (BD Biosciences) and were then allowed to incubate for 30 min at 4° C. Samples were spun down (500 g, 5 min, 4° C.) and resuspended in 200 μl of Perm/Wash buffer (BD Biosciences), this was repeated one more time. Samples were then spun down (500 g, 5 min, 4° C.) and resuspended in 50 μl of the antibody cocktail in Perm/Wash buffer and allowed to incubate for 30 min at room temperature in the dark. 200 μl of the Perm/Wash buffer was then added and both plates were spun down (500 g, 5 min, 4° C.) and resuspended in 200 μl of Perm/Wash buffer. This was followed by a final centrifuge step (500 g, 5 min, 4° C.), samples were then resuspended in 200 μl of FACS buffer.

IVIS imaging. Animals were anesthetized in an induction chamber using isoflurane ($O_2$ 1.5 L/min) and injected intraperitoneally with D-luciferin (300 ug/mL, 200 uL; PerkinElmer). Animals were then transferred to the IVIS manifold (IVIS Lumina K Series III, PerkinElmer) where they were kept under isoflurane anesthesia (0.25 L/min) and maintained warm on a heated stage. Animals were imaged with an XFOV-24 lens (FOV-E, 12.5 mm). Photographs (input settings) and luminescent images (settings) were acquired using the Imaging Wizard feature on the Live Imaging software (PerkinElmer). Luminescent exposures were set to 1, 5 and 15 seconds with the binning set at medium, the excitation set to block, the EM gain set to off, heights set at Mouse adjusted heights, with 0-second delays between acquisitions. Animals were imaged at 5 & 10 minutes after D-Luciferin injection.

Capsule explant testing. Five explanted capsules (n=5) from each group were added into individual wells in a 96-well plate. 200 ul of respective cell media was added to each well and after 24 hours of incubation, an ELISA per each expressed cytokine was run on the supernatant collected from the well. All samples were run in triplicate.

Statistics. Statistical analyses were conducted using Prism7 two-way ANOVA, multiple comparisons methods for IVIS imaging data analyses. ELISA data replicates were analyzed using paired student t-test methods. Outliers in replicates were identified using Grubb's tests and accounted for in standard error means or standard deviations when included.

Example 7: In Vivo Efficacy in a Mouse Model of Colorectal Cancer

Figures 10A, 10B, 10C, 10D, 10E, 10F, 10G, 10H:
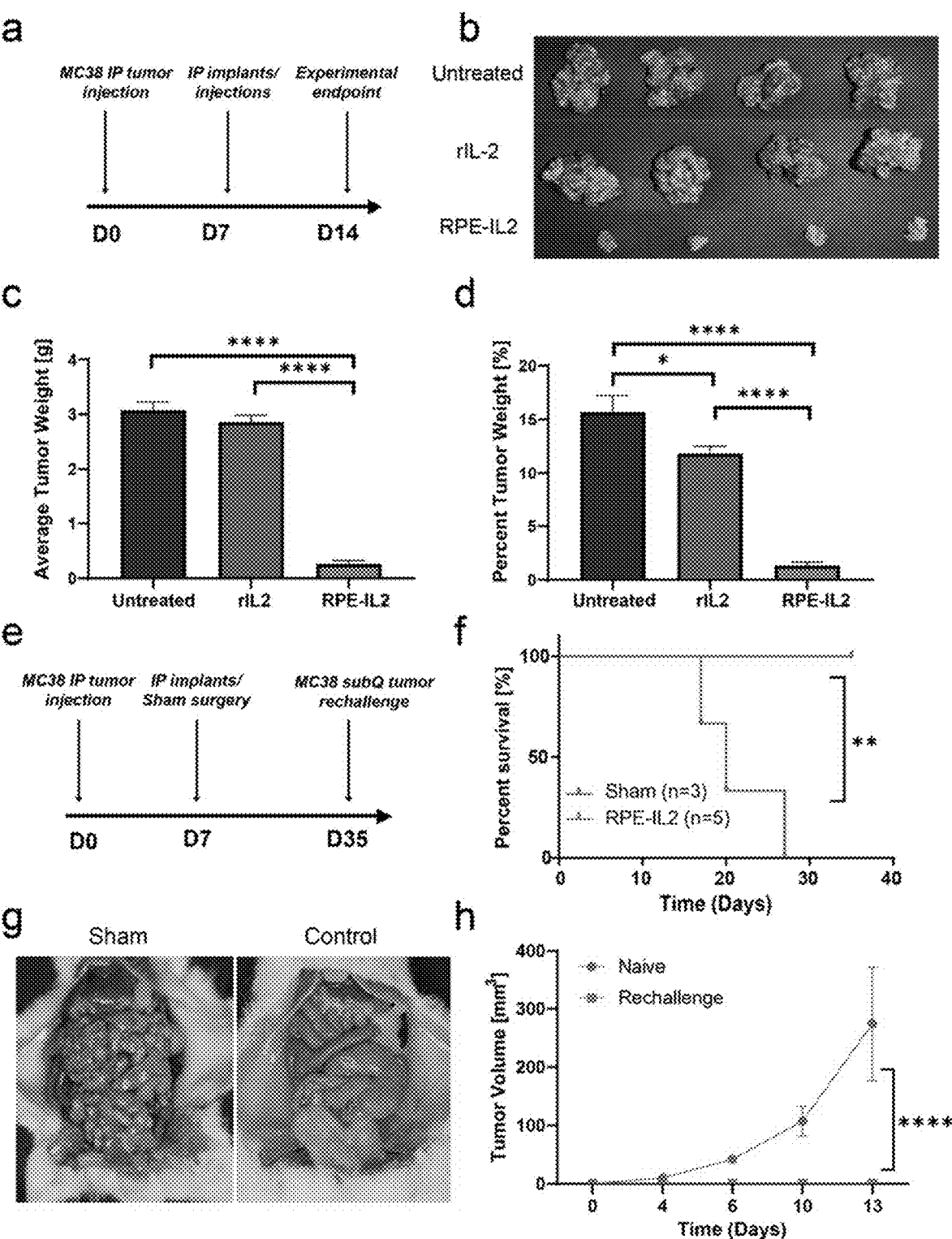
FIGS. 10A-10H show cytokine secretion in exemplary implantable constructs in a mouse MC38 colorectal cancer model and protection of recurrence.

To test the efficacy of exemplary implantable constructs in a mouse model of colorectal cancer, a mix of male and female B6 mice were injected in the IP space with MC38 cells (FIG. 10A) at a cell density of $1 \times 10^6$/mouse. 6 days post IP injections, animals were randomly divided into groups and surgically implanted with RPE-IL2 capsules or injected IP with recombinant IL-2 at a dose of 250,000 IU/day for 3 days and then monitored for 7 days. One week after treatment, the mice were sacrificed and the tumors were imaged (FIG. 10B) and weighed using an analytical balance. While the average weight of the mice in each of the three groups was similar, there was a significant difference in the weight of the tumors extracted from the mice. As shown in (FIG. 10C), the tumors in the untreated group as well as the sham surgery group weighed on average 3.1 g and 2.9 g, respectively. In contrast, the tissue extracted from the RPE-IL2 capsule group does not appear similar in color nor vascularity to the other groups and weighs more than 10× less than the other tumors (FIGS. 10B, 10D). A survival study was also conducted to study the duration of the anti-tumor affect provided by the RPE-IL2 capsules. A mix of male and female B6 mice were injected in the IP space with MC38 cells at a cell density of $1 \times 10^6$/mouse. As described above, 6 days post IP injections, animals were randomly stratified into two groups and either surgically implanted with core shell capsules or subjected to sham surgery. The survival study was terminated 8 days after the last sham mouse reached humane endpoint 35 (FIG. 10C) and 27 days post injection for RPE-IL2 capsule and sham group, respectively (FIG. 10F). At day 35 all RPE-IL2 MC38 injected mice were tumor free.

To rechallenge these mice, eight naïve mice and all five of the MC38 tumor free RPE-IL2 mice were injected subcutaneously with $5 \times 10^5$ MC38 cells and monitored until the naïve mice reached critical tumor volume (15 mm diameter) and had to be euthanized. After nearly two weeks, zero of the five RPE-IL2 mice developed a subcutaneous tumor while five out of the eight naïve mice developed visible tumor just four days post tumor injection (FIG. 10H). These results suggest that in addition to increasing activation and proliferation of CD8+ T cells, RPE-IL2 treatment also aids in development of memory T cells that prevent secondary tumors from developing.

Example 8: In Vivo Efficacy in a Mouse Model of Pancreatic Cancer

Figure 11A:
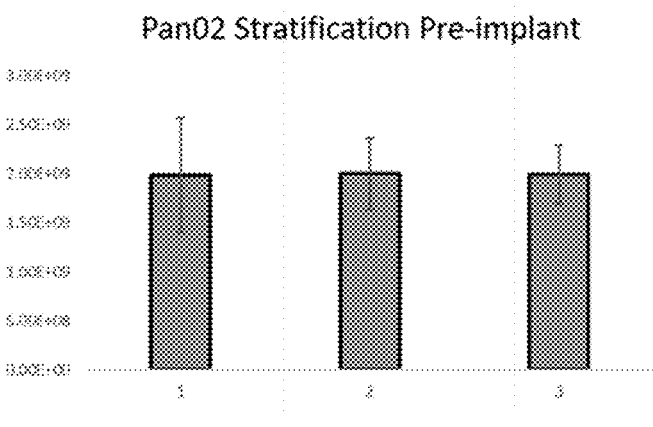
FIGS. 11A-11B show cytokine secretion in exemplary implantable constructs in a mouse pancreatic cancer model and reduction of tumor size.
Figure 11B:
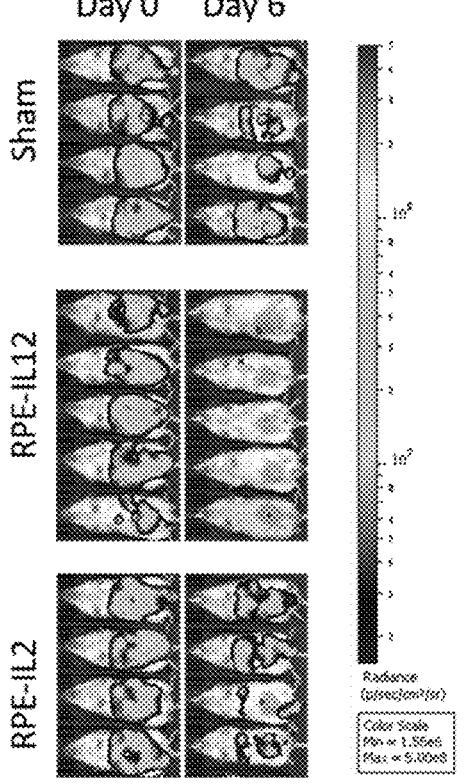

To test the efficacy of exemplary implantable constructs in pancreatic cancer, albino B6 mice (Jackson Labs) were injected with Pan02-F Luc cells. 5e6 Pan02-F Luc cells (suspended in saline) were intraperitoneally injected to the lower right abdomen of the mice. Prior to injection of implantable constructs expressing native IL-2, animals were all weighed, ear punch identified, and shaved along their abdomen. The abdomen was cleaned three times using 70% isopropyl alcohol followed by Betadine Surgical Scrub (7.5% povidone-iodine; Patterson Vet). A surgical blade (15T; Sklar) was used to cut a 0.5-0.75 cm midline incision through the skin and the linea alba into the abdomen. 1.5 mm implantable constructs were introduced into the peritoneal cavity. The abdominal muscle was closed by suturing with 5-0 Ethicon black PDS-absorbable sutures. The external skin layer was closed with PDS suture as previously described. After the surgery, the animals were put back in the cage to recover on a heating pad and monitored until ambulating. The animals were tracked for tumor growth or reduction using small animal IVIS imaging 1×/week. The results indicate that locally delivered native IL-12 via the implantable constructs described herein can reduce pancreatic cancer tumor burden in just 6 days (FIGS. 11A-B).

TABLE 1

| Cytokine Name | Sequences used |
| --- | --- |
| mIL-2<br>SEQ ID NO: 1 | ATGTACAGCATGCAGCTCGCATCCTGTGTCACATTGACACTTGTGCTCCTTGTCAACAGC<br>GCACCCACTTCAAGCTCCACTTCAAGCTCTACAGCGGAAGCACAGCAGCAGCAGCAGCA<br>GCAGCAGCAGCAGCAGCAGCACCTGGAGCAGCTGTTGATGGACCTACAGGAGCTCCTG<br>AGCAGGATGGAGAATTACAGGAACCTGAAACTCCCCAGGATGCTCACCTTCAAATTTTA<br>CTTGCCCAAGCAGGCCACAGAATTGAAAGATCTTCAGTGCCTAGAAGATGAACTTGGAC<br>CTCTGCGGCATGTTCTGGATTTGACTCAAAGCAAAAGCTTTCAATTGGAAGATGCTGAG<br>AATTTCATCAGCAATATCAGAGTAACTGTTGTAAAACTAAAGGGCTCTGACAACACATTT<br>GAGTGCCAATTCGATGATGAGTCAGCAACTGTGGTGGACTTTCTGAGGAGATGGATAG<br>CCTTCTGTCAAAGCATCATCTCAACAAGCCCTCAATAA |
| hIL-2<br>SEQ ID NO: 2 | ATGTACAGGATGCAACTCCTGTCTTGCATTGCACTAAGTCTTGCACTTGTCACAAACAGT<br>GCACCTACTTCAAGTTCTACAAAGAAAACACAGCTACAACTGGAGCATTTACTGCTGGAT<br>TTACAGATGATTTTGAATGGAATTAATAATTACAAGAATCCCAAACTCACCAGGATGCTC<br>ACATTTAAGTTTTACATGCCCAAGAAGGCCACAGAACTGAAACATCTTCAGTGTCTAGAA<br>GAAGAACTCAAACCTCTGGAGGAAGTGCTAAATTTAGCTCAAAGCAAAAACTTTCACTT<br>AAGACCCAGGGACTTAATCAGCAATATCAACGTAATAGTTCTGGAACTAAAGGGATCTG<br>AAACAACATTCATGTGTGAATATGCTGATGAGACAGCAACCATTGTAGAATTTCTGAAC<br>AGATGGATTACCTTTTGTCAAAGCATCATCTCAACACTGACTTGA |
| mIL-7<br>SEQ ID NO: 3 | ATGTTCCATGTTTCTTTTAGATATATCTTTGGAATTCCTCCACTGATCCTTGTTCTGCTGCC<br>TGTCACATCATCTGAGTGCCACATTAAAGACAAAGAAGGTAAAGCATATGAGAGTGTAC<br>TGATGATCAGCATCGATGAATTGGACAAAATGACAGGAACTGATAGTAATTGCCCGAAT<br>AATGAACCAAACTTTTTTAGAAAACATGTATGTGATGATACAAAGGAAGCTGCTTTTCTA<br>AATCGTGCTGCTCGCAAGTTGAAGCAATTTCTTAAAATGAATATCAGTGAAGAATTCAAT<br>GTCCACTTACTAACAGTATCACAAGGCACACAAACACTGGTGAACTGCACAAGTAAGGA<br>AGAAAAAAACGTAAAGGAACAGAAAAAGAATGATGCATGTTTCCTAAAGAGACTACTG<br>AGAGAAATAAAAACTTGTTGGAATAAAATTTTGAAGGGCAGTATATAA |
| hIL-7<br>SEQ ID NO: 4 | ATGTTCCATGTTTCTTTTAGGTATATCTTTGGACTTCCTCCCCTGATCCTTGTTCTGTTGCC<br>AGTAGCATCATCTGATTGTGATTTGAAGGTAAAGATGGCAAACAATATGAGAGTGTTC<br>TAATGGTCAGCATCGATCAATTATTGGACAGCATGAAAGAAATTGGTAGCAATTGCCTG<br>AATAATGAATTTAACTTTTTTAAAAGACATATCTGTGATGCTAATAAGGAAGGTATGTTT<br>TTATTCCGTGCTGCTCGCAAGTTGAGGCAATTTCTTAAAATGAATAGCACTGGTGATTTT<br>GATCTCCACTTATTAAAAGTTTCAGAAGGCACAACAATACTGTTGAACTGCACTGGCCAG<br>GTTAAAGGAAGAAAACCAGCTGCCCTGGGTGAAGCCCAACCAACAAAGAGTTTGGAAG<br>AAAATAAATCTTTAAAGGAACAGAAAAAACTGAATGACTTGTGTTTCCTAAAGAGACTA<br>TTACAAGAGATAAAAACTTGTTGGAATAAAATTTTGATGGGCACTAAAGAACACTGA |
| mIL-12 | SEQ ID NO: 5<br>ATGGTCAGCGTTCCAACAGCCTCACCCTCGGCATCCAGCAGCTCCTCTCAGTGCCGGTCC<br>AGCATGTGTCAATCACGCTACCTCCTCTTTTTGGCCACCCTTGCCCTCCTAAACCACCTCA<br>GTTTGGCCAGGGTCATTCCAGTCTCTGGACCTGCCAGGTGTCTTAGCCAGTCCCGAAACC<br>TGCTGAAGACCACAGATGACATGGTGAAGACGGCCAGAGAAAAACTGAAACATTATTC<br>CTGCACTGCTGAAGACATCGATCATGAAGACATCACACGGGACCAAACCAGCACATTGA<br>AGACCTGTTTACCACTGGAACTACACAAGAACGAGAGTTGCCTGGCTACTAGAGAGACT<br>TCTTCCACAACAAGAGGGAGCTGCCTGCCCCCACAGAAGACGTCTTTGATGATGACCCT<br>GTGCCTTGGTAGCATCTATGAGGACTTGAAGATGTACCAGACAGAGTTCCAGGCCATCA<br>ACGCAGCACTTCAGAATCACAACCATCAGCAGATCATTCTAGACAAGGGCATGCTGGTG<br>GCCATCGATGAGCTGATGCAGTCTCTGAATCATAATGGCGAGACTCTGCGCCAGAAACC<br>TCCTGTGGGAGAAGCAGACCCTTACAGAGTGAAAATGAAGCTCTGCATCCTGCTTCACG<br>CCTTCAGCACCCGCGTCGTGACCATCAACAGGGTGATGGGCTATCTGAGCTCCGCCTGA<br>SEQ ID NO: 6<br>ATGTGTCCTCAGAAGCTAACCATCTCCTGGTTTGCCATCGTTTTGCTGGTGTCTCCACTCA<br>TGGCCATGTGGGAGCTGGAGAAAGACGTTTATGTTGTAGAGGTGGACTGGACTCCCGA<br>TGCCCCTGGAGAAACAGTGAACCTCACCTGTGACACGCCTGAAGAAGATGACATCACCT<br>GGACCTCAGACCAGAGACATGGAGTCATAGGCTCTGGAAAGACCCTGACCATCACTGTC<br>AAAGAGTTTCTAGATGCTGGCCAGTACACCTGCCACAAAGGAGGCGAGACTCTGAGCC<br>ACTCACATCTGCTGCTCCACAAGAAGGAAAATGGAATTTGGTCCACTGAAATTTTAAAAA |

TABLE 1-continued

| Cytokine Name | Sequences used |
|---|---|

ATTTCAAAAACAAGACTTTCCTGAAGTGTGAAGCACCAAATTACTCCGGACGGTTCACGT
GCTCATGGCTGGTGCAAAGAAACATGGACTTGAAGTTCAACATCAAGAGCAGTAGCAG
TTCCCCTGACTCTCGGGCAGTGACATGTGGAATGGCGTCTCTGTCTGCAGAGAAGGTCA
CACTGGACCAAAGGGACTATGAGAAGTATTCAGTGTCCTGCCAGGAGGATGTCACCTGC
CCAACTGCCGAGGAGACCCTGCCCATTGAACTGGCGTTGGAAGCACGGCAGCAGAATA
AATATGAGAACTACAGCACCAGCTTCTTCATCAGGGACATCATCAAACCAGACCCGCCC
AAGAACTTGCAGATGAAGCCTTTGAAGAACTCACAGGTGGAGGTCAGCTGGGAGTACC
CTGACTCCTGGAGCACTCCCCATTCCTACTTCTCCCTCAAGTTCTTTGTTCGAATCCAGCG
CAAGAAAGAAAGATGAAGGAGACAGAGGAGGGGTGTAACCAGAAAGGTGCGTTCCT
CGTAGAGAAGACATCTACCGAAGTCCAATGCAAAGGCGGGAATGTCTGCGTGCAAGCT
CAGGATCGCTATTACAATTCCTCATGCAGCAAGTGGGCATGTGTTCCCTGCAGGGTCCG
ATCCTAG hIL-12       SEQ ID NO: 7
ATGTGGCCCCCTGGGTCAGCCTCCCAGCCACCGCCCTCACCTGCCGCGGCCACAGGTCT
GCATCCAGCGGCTCGCCCTGTGTCCCTGCAGTGCCGGCTCAGCATGTGTCCAGCGCGCA
GCCTCCTCCTTGTGGCTACCCTGGTCCTCCTGGACCACCTCAGTTTGGCCAGAAACCTCC
CCGTGGCCACTCCAGACCCAGGAATGTTCCCATGCCTTCACCACTCCCAAAACCTGCTGA
GGGCCGTCAGCAACATGCTCCAGAAGGCCAGACAAACTCTAGAATTTTACCCTTGCACTT
CTGAAGAGATTGATCATGAAGATATCACAAAAGATAAAACCAGCACAGTGGAGGCCTG
TTTACCATTGGAATTAACCAAGAATGAGAGTTGCCTAAATTCCAGAGAGACCTCTTTCAT
AACTAATGGGAGTTGCCTGGCCTCCAGAAAGACCTCTTTTATGATGGCCCTGTGCCTTAG
TAGTATTTTATGAAGACTTGAAGATGTACCAGGTGGAGTTCAAGACCATGAATGCAAAGC
TTCTGATGGATCCTAAGAGGCAGATCTTTCTAGATCAAAACATGCTGGCAGTTATTGATG
AGCTGATGCAGGCCCTGAATTTCAACAGTGAGACTGTGCCACAAAAATCCTCCCTTGAA
GAACCGGATTTTTATAAAACTAAAATCAAGCTCTGCATACTTCTTCATGCTTTCAGAATTC
GGGCAGTGACTATTGATAGAGTGATGAGCTATCTGAATGCTTCCTAA
SEQ ID NO: 8
ATGTGTCACCAGCAGTTGGTCATCTCTTGGTTTTCCCTGGTTTTTCTGGCATCTCCCCTCG
TGGCCATATGGGAACTGAAGAAAGATGTTTATGTCGTAGAATTGGATTGGTATCCGGAT
GCCCCTGGAGAAATGGTGGTCCTCACCTGTGACACCCCTGAAGAAGATGGTATCACCTG
GACCTTGGACCAGAGCAGTGAGGTCTTAGGCTCTGGCAAAACCCTGACCATCCAAGTCA
AAGAGTTTGGAGATGCTGGCCAGTACACCTGTCACAAAGGAGGCGAGGTTCTAAGCCA
TTCGCTCCTGCTGCTTCACAAAAAGGAAGATGGAATTTGGTCCACTGATATTTTAAAGGA
CCAGAAAGAACCCAAAAATAAGACCTTTCTAAGATGCGAGGCCAAGAATTATTCTGGAC
GTTTCACCTGCTGGTGGCTGACGACAATCAGTACTGATTTGCATTCAGTGTCAAAAGCA
GCAGAGGCTCTTCTGACCCCCAAGGGGTGACGTGCGGAGCTGCTACACTCTCTGCAGAG
AGAGTCAGAGGGGACAACAAGGAGTATGAGTACTCAGTGGAGTGCCAGGAGGACAGT
GCCTGCCCAGCTGCTGAGGAGAGTCTGCCCATTGAGGTCATGGTGGATGCCGTTCACAA
GCTCAAGTATGAAAACTACACCAGCAGCTTCTTCATCAGGGACATCATCAAACCTGACCC
ACCCAAGAACTTGCAGCTGAAGCCATTAAAGAATTCTCGGCAGGTGGAGGTCAGCTGG
GAGTACCCTGACACCTGGAGTACTCCACATTCCTACTTCTCCCTGACATTCTGCGTTCAG
GTCCAGGGCAAGAGCAAGAGAGAAAAGAAAGATAGAGTCTTCACGGACAAGACCTCA
GCCACGGTCATCTGCCGCAAAAATGCCAGCATTAGCGTGCGGGCCCAGGACCGCTACTA
TAGCTCATCTTGGAGCGAATGGGCATCTGTGCCCTGCAGTTAG mIL-15       ATGAAAATTTTGAAACCATATATGAGGAATACATCCATCTCGTGCTACTTGTGTTTCCTTC
SEQ ID NO: 9   TAAACAGTCACTTTTTAACTGAGGCTGGCATTCATGTCTTCATTTTGGGCTGTGTCAGTGT
AGGTCTCCCTAAAACAGAGGCCAACTGGATAGATGTAAGATATGACCTGGAGAAAATT
GAAAGCCTTATTCAATCTATTCATATTGACACCACTTTATACACTGACAGTGACTTTCATC
CCAGTTGCAAAGTTACTGCAATGAACTGCTTTCTCCTGGAATTGCAGGTTATTTTACATG
AGTACAGTAACATGACTCTTAATGAAACAGTAAGAAACGTGCTCTACCTTGCAAACAGC
ACTCTGTCTTCTAACAAGAATGTAGCAGAATCTGGCTGCAAGGAATGTGAGGAGCTGGA
GGAGAAAACCTTCACAGAGTTTTTGCAAAGCTTTATACGCATTGTCCAAATGTTCATCAA
CACGTCCTGA hIL-15       ATGAGAATTTCGAAACCACATTTGAGAAGTATTTCCATCCAGTGCTACTTGTGTTTACTTC
SEQ ID NO: 10  TAAACAGTCATTTTCTAACTGAAGCTGGCATTCATGTCTTCATTTTGGGCTGTTTCAGTGC
AGGGCTTCCTAAAACAGAAGCCAACTGGGTGAATGTAATAAGTGATTTGAAAAAAATTG
AAGATCTTATTCAATCTATGCATATTGATGCTACTTTATATACGGAAGTGATGTTCACCC
CAGTTGCAAAGTAACAGCAATGAAGTGCTTTCTCTTGGAGTTACAAGTTATTTCACTTGA
GTCCGGAGATGCAAGTATTCATGATACAGTAGAAAATCTGATCATCCTAGCAAACAACA
GTTTGTCTTCTAATGGGAATGTAACAGAATCTGGATGCAAAGAATGTGAGGAACTGGAG
GAAAAAAATATTAAAGAATTTTTGCAGAGTTTTGTACATATTGTCCAAATGTTCATCAAC
ACTTCTTGA

Firefly      ATGGAAGACGCCAAAAACATAAAGAAAGGCCCGGCGCCATTCTATCCGCTAGAGGATG
Luciferase   GAACCGCTGGAGAGCAACTGCATAAGGCTATGAAGAGATACGCCCTGGTTCCTGGAAC
SEQ ID NO: 11  AATTGCTTTTACAGATGCACATATCGAGGTGAACATCACGTACGCGGAATACTTCGAAAT
GTCCGTTCGGTTGGCAGAAGCTATGAAACGATATGGGCTGAATACAAATCACAGAATCG
TCGTATGCAGTGAAAACTCTCTTCAATTCTTTATGCCGGTGTTGGGCGCGTTATTTATCG
GAGTTGCAGTTGCGCCCGCGAACGACATTTATAATGAACGTGAATTGCTCAACAGTATG
AACATTTCGCAGCCTACCGTAGTGTTTGTTTCCAAAAAGGGGTTGCAAAAAATTTTGAAC
GTGCAAAAAAAATTACCAATAATCCAGAAAATTATTATCATGGATTCTAAAACGGATTAC
CAGGGATTTCAGTCGATGTACACGTTCGTCACATCTCATCTACCTCCCGGTTTTAATGAAT
ACGATTTTGTACCAGAGTCCTTTGATCGTGACAAAACAATTGCACTGATAATGAACTCCT
CTGGATCTACTGGGTTACCTAAGGGTGTGGCCCTTCCGCATAGAACTGCCTGCGTCAGA
TTCTCGCATGCCAGAGATCCTATTTTTGGCAATCAAATCATTCCGGATACTGCGATTTTAA TABLE 1-continued

| Cytokine Name | Sequences used |
| --- | --- |

GTGTTGTTCCATTCCATCACGGTTTTGGAATGTTTACTACACTCGGATATTTGATATGTGG
ATTTCGAGTCGTCTTAATGTATAGATTTGAAGAAGAGCTGTTTTTACGATCCCTTCAGGA
TTACAAAATTCAAAGTGCGTTGCTAGTACCAACCCTATTTTCATTCTTCGCCAAAAGCACT
CTGATTGACAAATACGATTTATCTAATTTACACGAAATTGCTTCTGGGGGCGCACCTCTT
TCGAAAGAAGTCGGGGAAGCGGTTGCAAAACGCTTCCATCTTCCAGGGATACGACAAG
GATATGGGCTCACTGAGACTACATCAGCTATTCTGATTACACCCGAGGGGGATGATAAA
CCGGGCGCGGTCGGTAAAGTTGTTCCATTTTTTGAAGCGAAGGTTGTGGATCTGGATAC
CGGGAAAACGCTGGGCGTTAATCAGAGAGGCGAATTATGTGTCAGAGGACCTATGATT
ATGTCCGGTTATGTAAACAATCCGGAAGCGACCAACGCCTTGATTGACAAGGATGGATG
GCTACATTCTGGAGACATAGCTTACTGGGACGAAGACGAACACTTCTTCATAGTTGACC
GCTTGAAGTCTTTAATTAAATACAAAGGATACCAGGTGGCCCCCGCTGAATTGGAGTCG
ATATTGTTACAACACCCCAACATCTTCGACGCGGGCGTGGCAGGTCTTCCCGACGATGA
CGCCGGTGAACTTCCCGCCGCCGTTGTTGTTTTGGAGCACGGAAAGACGATGACGGAAA
AAGAGATCGTGGATTACGTCGCCAGTCAAGTAACAACCGCGAAAAAGTTGCGCGGAGG
AGTTGTGTTTGTGGACGAAGTACCGAAAGGTCTTACCGGAAAACTCGACGCAAGAAAA
ATCAGAGAGATCCTCATAAAGGCCAAGAAGGGCGGAAAGTCCAAATTGTAA

Metridia
Luciferase
SEQ ID NO: 12

ATGGACATCAAGGTGGTGTTCACCCTGGTGTTCAGCGCCCTGGTGCAGGCCAAGAGCAC
CGAGTTCGACCCCAACATCGACATCGTGGGCCTGGAAGGCAAGTTCGGCATCACCAACC
TGGAAACCGACCTGTTCACCATCTGGGAGACCATGGAAGTGATGATCAAGGCCGACATC
GCCGACACCGACCGGGCCAGCAACTTCGTGGCCACCGAGACCGACGCCAACCGGGGCA
AGATGCCCGGCAAGAAGCTGCCCCTGGCCGTCATCATGGAAATGGAAGCCAACGCCTTC
AAGGCCGGCTGCACCCGGGGCTGCCTGATCTGCCTGAGCAAGATCAAGTGCACCGCCA
AGATGAAGGTGTACATCCCCGGCAGGTGCCACGACTACGGCGGCGACAAGAAAACCGG
CCAGGCCGGCATCGTGGGCGCCATCGTGGACATCCCCGAGATCAGCGGCTTCAAAGAA
ATGGCCCCCATGGAACAGTTCATCGCCCAGGTGGACAGATGCGCCAGCTGCACCACCGG
CTGCCTGAAGGGCCTGGCCAACGTGAAGTGCAGCGAGCTGCTGAAGAAGTGGCTGCCC
GACCGCTGCGCCAGCTTCGCCGACAAGATCCAGAAAGAGGTGCACAACATCAAGGGCA
TGGCCGGCGACAGGTGA

Example 9: Materials and Methods

Materials. Cell culture media and associated reagents, as well as transfection medias were purchased through Fisher Scientific. The aRPE-19 cell line was purchased from ATCC. Lipofection reagents (lipofectamine 3000) and selection media (puromycin) were purchased from Invitrogen. Expression vectors and helper plasmids were developed and bought through VectorBuilder. CellTiter-Glo was purchased through Promega. TrypanBlue and Live Dead stains were purchased through Fisher Scientific, as well as fluorescence microscopes. The encapsulation machine contained syringe pumps from Harvard Apparatus, and co-axial nozzles from Rame-Hart. Alginate compounds were purchased through PRONOVA. All animals were purchased from Jackson Labs.

Cell Culture and Engineering. ID8/MOSEC cells were obtained commercially from EMD Millipore, Sigma. Human aRPE-19 cells were obtained from ATCC. aRPE-19 cells were cultured using Dulbecco's Modified Eagle Medium (DMEM/F-12), with 10% Non-heat inactivated Fetal Bovine Serum (FBS) and 1% antibiotic-antimycotic (AA). When cells reached 70-90% confluency culture medium was discarded, and cells were briefly washed with 5 ml's of DPBS. Washing solution was aspirated and followed by 5 ml's TrypLE to disperse the cell layer. Cells were incubated for 3 minutes, then observed under a microscope to ensure detachment. 7 mL's of complete growth medium were added to the flask to stop the TrypLE reaction. The cell suspension was transferred to a 15 mL confocal tube and centrifuged for 5 minutes at 250G. The supernatant was aspirated, and the pellet resuspended. Cells were resuspended in 1 mL of complete media and redistributed in a sterile T-75 flasks at the desired concentration. 13 mL's complete 5 media were added to the flask and cells were incubated at 37° C. in a 5% CO2 humidified atmosphere. The media was changed 3 times weekly. Media used for B16-F10 was DME/F-12, 10% FBS, 1% antibiotic-antimycotic (AA). Media used for ID8 was DMEM High Glucose, 4% FBS, 1% AA, and 1% ITS. Plasmids for lentiviral transduction and lipofectamine transfections of all cells used were designed and purchased from VectorBuilder in DNA MaxiPrep form. ARPE-19 cells were engineered to express mouse IL2 and firefly luciferase. ID8/MOSEC cells were engineered to express firefly luciferase. Engineered cells were assayed for linearity between luciferase expression and cell number using IVIS imaging (methods followed small animal imaging described below.) ARPE cytokine expressing cell lines were assayed for cell viability and changes in doubling time post-transfection/transduction using traditional cell subculture methods and trypan blue based counting methods.

Cell Transfection/Lipofection. For transfection of native mouse IL-2, aRPE-19 cells that had been passaged four times were seeded into 6 well plates at a concentration of 500,000 cells/well with 3 mL complete media. The plate was incubated overnight at 37° C. in a 5% CO2 humidified atmosphere. 24 hours following seeding, culture medium was aspirated, and each well was primed with 2 ml Opti-MEM serum free medium. In an Eppendorf tube a 2:1 ratio of expression vector to helper plasmid was added to 125 μl of Opti-MEM, with 6 ul P3000. This solution was incubated at room temperature for 5 minutes. In a new Eppendorf tube 125 μl Opti-MEM was mixed with 3.75 μl of lipofectamine3000. Values were adjusted based on the number of wells. The Eppendorf tubes containing lipofectamine3000 were combined with the DNA complex and incubated at room temperature for 15 minutes. Opti-MEM used to prime the wells was discarded, and 2.5 ml fresh Opti-MEM was added to each well. The DNA-lipid complexes were then added—250 μl per well—to five of six wells with the last well remaining as a control. After incubation at 37° C. for 4 hours, the transfection media was replaced with fresh culture media containing 10% FBS, and 1% AA. Four days after transfection, culture medium was aspirated, and cells were transferred to a T-75 flask, with 15 ml's of DMEM with 10% FBS, 1% AA, and 50 μl/500 ml puromycin. On the fourth day, cells were selected for expression with puromycin for one week and then maintain using normal cell culture techniques.

Cell transduction. ID8/MOSEC Cells were transduced using a standard 3rd generation lentivirus protocol. Lentivirus was produced by transfection of 3 packaging plasmids (pMLg/PRRE, pRSV-Rev and pMD2.g) together with an expression vector in HEK293T cells. 6-8 hours after transfection, the cell media was replaced with new media and cells were cultured for 36-48 hours. The lentivirus was concentrated and used with polybrene to transduce ID8/MOSEC cells which had been plated the day before and were at 70-80% confluency. After a 24-hour incubation with the virus, the media was changed, and the cells were cultured for 3 days. On the fourth day, cells were selected for expression with puromycin for one week and then maintain using normal cell culture techniques.

Core Shell Cell Encapsulation. Alginate hydrogel spheres were synthesized using a custom-built, two-fluid co-axial electrostatic spraying device. The device consisted of a voltage generator that was attached to the tip of a co-axial needle and grounded to a 1:4 barium chloride: mannitol crosslinking bath. The co-axial needle was fed by two separate syringes containing 1.4% alginate solutions that were diluted in 0.9% saline. In order to suspend cells in alginate, cells that had reached 70-90% confluency were removed of supernatant and washed with 5 ml's of DPBS. The washing solution was aspirated and followed by 5 ml's TrypLE to disperse the cell layer. Cells were incubated for 3 minutes, then observed under a microscope to ensure detachment. 7 mL's of complete growth medium was added to the flask to stop the TrypLE reaction. The cell suspension was transferred to a 50 ml conical tube and centrifuged for 5 minutes at 250G. The supernatant was aspirated, and the palette was broken. The desired volume of SLG20 alginate was added to the cells and pulled up by a 5 ml Luer lock syringe. Syringes containing SLG20 alginate were placed in two separate syringe pumps that were fed into a co-axial nozzle which was then suspended over 150 ml of the crosslinking bath; SLG20 fed into the horizontal axis of the nozzle which made the shell, while SLG20 with cells fed into the vertical axis of the nozzle which made the core. Flow rates for each syringe were adjusted to a ratio of 5 ml/hr. Size of the capsules was maintained by adjusting the voltage on the generator; a voltage of −5.30 most consistently produced capsules that were 1.5 mm in diameter. Capsules were decanted in order to separate them from the crosslinking bath. They were subsequently washed 3 times with HEPES buffer, and 3 times with complete cell medium. Finally, encapsulated cells were transferred to a T-25 flask containing 6 mls of complete media and maintained with normal cell culture techniques. Following encapsulation, a subset of cells were washed with 5 ml DPBS and stained using a stock 2 µM calcein AM and 4 µM EthD-1 in DPBS. The sample was incubated for 20 minutes and imaged using a fluorescence microscope. 20 capsules were imaged from each sample group of encapsulated cells and examined for live and dead cells; a GFP filter was used to capture live cells and a Texas Red filter was used to capture dead cells.

Enzyme-Linked Immunosorbent Assay. Cells from each group were grown up into a T¬150 flask in DMEM media with 10% FBS, 1% Penstrep, and 0.5 µU500 ml puromycin. At confluency, culture media was aspirated and 10 ml TrypLE was added. Cells were incubated for 3 minutes at 37° C. in a 5% CO2 humidified atmosphere. Once the cell layer was dispersed, 10 ml's complete media was added to stop the reaction. The cell suspension was transferred to a 50 ml conical tube and centrifuged at 250G for 5 minutes. The supernatant was aspirated, and cells were re-suspended in 1 ml complete media. Cell concentration was counted using a Countess™ hemocytometer. The volume required to achieve a concentration of 10,000 cells in 200 ul was calculated based on the concentration of live cells in the sample. Of the remaining cell suspension volume, 8 million cells were resuspended in 1 ml alginate to be synthesized into core shell capsules. All groups were incubated for 24 hours at 37° C. in a 5% CO2 humidified atmosphere. Cell supernatant was collected from each well and transferred to a 2 ml microfuge tube at the 24-hour time period. Assays were run on the BioLegend Mouse IL2 ELISA Kit (Cat. No. 431007). The assay was run according to protocols provided by the company.

Capsule explant analysis. Five explanted capsules (n=5) from each group were added into individual wells in a 96 well plate. 200 µl of respective cell media was added to each well and after 24 hours of incubation, an ELISA per each expressed cytokine was run on the supernatant collected from the well. All samples were run in triplicate.

T cell proliferation assay. An EasySep T Cell Isolation Kit (StemCell Technologies) and associated reagents and devices were used to isolate T cell from C57BL6 mouse spleens (Jackson Labs). Cells were plated in 96 well plates at 10,000 cells/well in 100 µl RPMI 1640. Cells were supplemented with 0.1, 1, 5 or 10 ng/mL of cell produced native IL2 or 1 or 10 ng/mL of recombinant IL-2 (Miltenyi). 24 or 72 hours after incubation at 37° C., cell proliferation (and viability) was measured using CellTiter-Glo Luminescent Cell Viability Assay (Promega). Flow Cytometry. Antibody cocktails: Anti-mouse CD4, CD8, CD25, CD3, CD19, FOXp3, and Ki67 were commercially obtained and resuspended in Perm/Wash buffers at vendor recommended dilutions (1:50, 1:100, 1:200, 1:400) per each antibody. All antibody cocktails were prepared the day of staining and maintained in the dark at 4° C. or in ice.

Sample Processing. All samples were maintained on ice or kept at 4° C. throughout the processing and staining procedures below.

Spleens: Spleens are mashed using pestles against a strainer. Spleen tissue samples were then washed three times using RPMI media (Gibco), spun down (2000 rpm, 3 min, RT) then resuspended in 3 mL of RBC lysis buffer (Sigma) and incubated for 10 min at room temperature. After incubation 10 mL of RPMI media is added to the spleen solution, the sample is mixed then spun down (2000 rpm, 3 min, RT) then resuspended in FACS buffer (PBS, 2% calf serum, 1 mM EDTA, 0.1% Sodium Azide) and counted for cell concentration using Trypan Blue (Thermo Fisher).

IP Fluid: Collected IP fluid (10 mL) is filtered through a 70 µm strainer, spun down (2000 rpm, 3 min, RT) then resuspended in 3 mL of RBC Lysis Buffer and left to incubate for 10 min at room temperature.

Blood Samples: RBC lysis buffer (2 parts) is added to the blood sample (1 part) and then vortexed. The sample is allowed to incubate for 3 min at room temperature. The sample is then spun down (15,000 rpm, 5 min, RT) then resuspended in 300 uL of FACS buffer, this wash step is repeated one more time followed by a final filtration step with a 40 micron cell strainer.

Tumor Samples: Tumors were processed using mouse tumor dissociation kits (Miltenyi Biotec; Cat. No 130-096-730). Dissociation protocols followed the product safety data sheet reported with the kit.

Sample Staining: Samples were plated into deep 96 well plates at a density of approximately 2.5 million cells/well. Plates were spun down (500 g, 5 min, RT) and resuspended in FACS buffer.

Extracellular Staining: Plates were spun down (500 g, 5 min, RT) and resuspended in 50 µL of Fc block buffer (0.25 ug of CD16/CD32 added per one million cells into 50 µL of FACS buffer). Plates were then left to incubate for 10 min on ice in the dark. 150 uL of cold FACS buffer was added and mixed with the suspension of Fc block solution. Samples were then split in half and aliquoted to a second deep 96 well plate. 100 µL of cold FACS buffer was added to each well for both deep 96 well plates followed by a centrifuge step (400 g, 5 min, 4° C.). Supernatants were removed from both plates and the pellets were resuspended in 50 µL of antibody cocktails. Samples were then allowed to stain for 30 min, at 4 C in the dark. Plates were then spun down (500 g, 5 min, 4° C.) and resuspended in 100 µL of cold FACS buffer, this wash step is repeated once more.

Intracellular Staining: Intracellular staining occurs immediately following extracellular staining Cell pellets in both plates were resuspended in 200 µL of a Fixation/Permeabilization solution (BD Biosciences) and were then allowed to incubate for 30 min at 4° C. Samples were spun down (500 g, 5 min, 4° C.) and resuspended in 200 µL of Perm/Wash buffer (BD Biosciences), this was repeated one more time. Samples were then spun down (500 g, 5 min, 4° C.) and resuspended in 50 uL of the antibody cocktail in Perm/Wash buffer and allowed to incubate for 30 min at room temperature in the dark. 200 ul of the Perm/Wash buffer was then added and both plates were spun down (500 g, 5 min, 4° C.) and resuspended in 200 uL of Perm/Wash buffer. This was followed by a final centrifuge step (500 g, 5 min, 4° C.), samples were then resuspended in 200 µL of FACS buffer.

Tumor implants. C57BL6, albino or nu/nu mice (Jackson Labs) were used for in vivo tumor regression study. All animal studies were performed based on the approval by Rice University IACUC. For subcutaneous model of melanoma, C57BL6 mice were subcutaneously injected with 5e5 B 16F10 cells. The cells were suspended in HBSS prior to injection. For IP tumor models of ID8/MOSEC-F Luc; 10e6 cells suspended in HBSS were intraperitoneally injected to the lower right abdomen of the C57BL6, albino or nu/nu female mice.

Tumor growth tracking. Subcutaneous Tumors: For subcutaneous B 16F10 the tumor size was measured using a digital caliper and tumor volume was calculated using the formula V=0.5*(height)*(width2). Intraperitoneal Tumors: Animals injected with ID8/MOSEC F-Luc cells were tracked every other day for 7-10 days before they were selected for implantation surgery, sham surgeries, or untreated control groups. After surgery, animals were tracked for tumor growth or reduction using small animal IVIS imaging 1× per week. Imaging methods are expanded below. Animal surgeries. Anesthesia and Analgesia. All procedures were conducted under anesthesia and treated with subsequent analgesia. Mice used in studies were anesthetized with isoflurane (1-4%) and oxygen (1-2 L) using a rodent anesthesia machine by tank induction followed by nose cone maintenance. Pedal withdrawal reflex was used to evaluate the depth of anesthesia for gas anesthesia before beginning any invasive procedure and respiration was monitored continuously to ensure sufficient anesthesia. Body temperatures were regulated during anesthesia and recovery through the use of water circulating heating pads. Importantly, the depth of anesthesia was continuously monitored throughout the surgeries.

Intraperitoneal (IP) surgical implantation of capsules. Animals were weighed, ear punch identified, and shaved along their abdomen prior to surgery. This was followed by one scrub with isopropyl alcohol followed by a second scrub with Betadine Surgical Scrub (7.5% povidone-iodine; Patterson Vet). These anti-septic scrubbing steps were repeated three times. A sharp surgical blade (15T; Sklar) was then used to cut a 0.5-0.75 cm midline incision through the skin and the linea alba into the abdomen. Capsule implants were introduced into the peritoneal cavity. The abdominal muscle was closed by suturing with 5-0 Ethicon black PDS-absorbable or other 5.0-6.0 monofilament absorbable sutures. The external skin layer was closed with PDS suture as previously described. IVIS imaging Animals were anesthetized in an induction chamber using isoflurane isoflurane (1-4%) and oxygen (1-2 L) and injected in the IP space with D-luciferin (300 µg/mL, 200 µL; PerkinElmer) Animals were then transferred to the IVIS manifold (IVIS Lumina K Series III, PerkinElmer) where they were kept under isoflurane anesthesia (0.25 L/min) and maintained warm on a heated stage. Animals were imaged with an XFOV-24 lens (FOV-E, 12.5 mm). Photographs and luminescent images were acquired using the Imaging Wizard feature on the Live Imaging software (PerkinElmer). Luminescent exposures were set to 1, 5 and 15 seconds with the binning set at medium, the excitation set to block, the EM gain set to off with 0-second delays between acquisitions. Animals were imaged at 5 & 10 minutes after D-Luciferin injection. Statistics. Statistical analysis was conducted using Prism? two-way ANOVA and one-way ANOVA, multiple comparisons methods for IVIS imaging data analysis. ELISA data replicates were analyzed using paired student t-test methods and where indicated with one-way ANOVA. Outliers in replicates were identified using Grubb's tests and accounted for in standard error means or standard deviations when included.

Example 10: Results and Conclusion

Here, the inventors sought to develop a cell-generated cytokine delivery system to enable high concentration tumor-adjacent delivery of native cytokines for peritoneal cancer therapy. Human retinal pigmented epithelial cell, ARPE-19 (RPE) were engineered to stably express IL-2, IL-7, IL-10 or IL-12 (FIG. 12a) using a PiggyBAC transposon system and non-viral lipid-based transfection. Key characteristics of the cytokines used in this study, such as molecular weight, structure, function and half-life were described.

The cytokines chosen have distinct chemical properties; however, using the inventors' plug and play cell engineering platforms the inventors can quickly develop these wide-ranging products within less than four weeks to enable rapid preclinical testing. The ease and speed of going from concept to pre-clinical testing is a significant advantage of over protein engineering or formulation strategies which could take many months to years to optimize35. RPE was chosen as the platform cell line because it is non-tumorigenic, displays contact inhibited growth characteristics, amendable to genetic modification, and had been previously used in human trials for delivery of therapeutics and shown to be safe. These engineered cells were subsequently encapsulated into alginate-based core-shell capsules using a coaxial needle and crosslinking bath (FIG. 12b). The inventors chose SLG20 grade of alginate to develop the inventors' system because it has been previously used in human clinical trials and shown to be safe and available in GMP grade 41, 42. Subsequent to encapsulation, the native cytokine factories are referred to as RPE-IL2, RPE-IL7, RPE-IL10 and RPE-IL12, respectively. Core-shell capsule design protects the encapsulated cells from the cells of the host immune system and allows the cells to persist in the body longer than injected free cells alone. The size and shape of these capsules was optimized to achieve 1.5 mm in diameter spherical particles by adjusting the flow rate of the alginate from both syringes. This size and shape was chosen because as previously reported spherical implants of this size were less prone to aggregation or embedding into scar tissue within the peritoneal cavity compared to their smaller counterparts. The shear stress associated with flowing through the coaxial needle did not affect their viability (FIG. 12c) or their ability to produce proteins. Cells remained viable inside the capsules for at least one month as determined by live/dead fluorescent staining post encapsulation over time. The encapsulated RPE cell line could be expanded in 2D culture but exhibited contact inhibition in 3D upon encapsulation and thus did not continue dividing inside of the capsules. This feature was critical for regulating the dose of cytokine per capsule post deployment.

Diffusion kinetics of these natural cytokines in vitro, protein production from a single capsule containing $3\times10^4$ cells was tracked for 1-, 2-, 4- and 24-hours using ELISA. For up to 4 hours, the protein release from each capsule was linear with $r^2$ values of 0.973, 0.995, 0.976 and 0.929 for RPE-IL2, RPE-IL7, RPE-IL10 and RPE-IL12, respectively, and thus followed first order kinetics (FIG. 12d). At a point between 4 and 24 hours, the diffusion kinetics lost linearity as the rate of protein degradation approached the rate of protein production. These results highlighted and reinforced the need for continuous production of new cytokines to maintain therapeutic protein levels over time in vivo[44].

To validate the ability of this platform to increase local cytokine concentrations in vivo, naïve C57BL6 mice were surgically implanted with 100 capsules in the IP cavity (IP space) for 24 hours. The IP fluid and blood were collected and assayed for protein production using ELISA (FIGS. 12e-h). For each of the tested cytokines (RPE-IL2, RPE-IL7, RPE-IL10, or RPE-IL12), the local concentration (IP space) was 100×, 64×, 38×, and 544×, respectively, higher than the systemic concentration (blood) demonstrating the ability of the inventors' platform to not only deliver native cytokines in vivo, but also to create a high local concentration of cytokines without greatly altering the circulating concentration. This critical delivery feature suggested the platform's ability to strategically activate local populations of immune cells without eliciting the toxicities associated with systemic administration. Because mouse models were used in this study, the murine version of each protein was used to engineer the RPE cells. However, comparable concentrations of the human version of this protein can also be produced to allow for this platform to be easily translated into human studies.

Differences in biological activity were assayed using isolated murine T-cells treated with either RPE-IL2 generated or recombinant IL-2 at a concentration of 1 and 10 ng/mL for 24 hours. RPE-IL2 was found to induce T cell proliferation 36× more than recombinant IL-2 (rIL2) at low (1 ng/mL) and 128× more at high (10 ng/mL) concentrations (FIG. 12i) demonstrating that RPE-IL2 was significantly more bioactive than rIL-2. Proliferation was also quantified at 72 hours and, the isolated T cells were still proliferating and cell proliferation was dose dependent.

To test the ability to tune local concentration of IL-2 delivered in vivo, the inventors varied the number of capsules within a given dose. Four doses of RPE-IL2 capsules, 10, 50, 100, 200, were implanted IP and the in vivo concentration of IL-2 was assayed via ELISA after 24 hours (FIG. 12j). The IP concentration of IL-2 increased with the number of capsules delivered and regardless of the number of capsules delivered and the IL-2 levels in the IP fluid were consistently at least 100× higher than the levels found in the blood. These results suggested that IL-2 dosing could be carefully controlled by adjusting the number of capsules given in a single dose.

To study the duration of exposure and concentration of IL-2 secretion from within the core shell capsules, 200 capsules of RPE-IL2 were implanted within the IP space of C57BL6 mice and allowed to remain for either 1d, 4d, 7d, 14d, 21d or 30d. At each time point, the mice were sacrificed and the capsules, blood and IP fluid were collected and assayed for IL-2 concentration using an ELISA. As shown in (FIG. 12k), the IL-2 concentration peaked 24 hours after implantation and remained well above the threshold for high affinity IL-2R binding for over 14 days before the capsules became coated by the host immune system[44]. Images of explanted capsules validated that the capsules became coated by the host immune cells overtime (FIG. 12l), corresponding with the reduction of measurable IL-2 concentration in both the blood and IP fluid and by day 21 the RPE-IL2 completely shut down. The natural foreign body response (FBR) to hydrogel microparticles has been previously shown to cause pericapsular overgrowth (PFO) on the surface of the capsules which leads to a slow decrease in pore size and eventual cell death when oxygen and nutrients cease to diffuse inside[43]. Although generally problematic, the inventors leveraged this natural phenomenon to rationally design a dosing regimen that benefited from PFO on the surface of the inventors' system to shut down cytokine production over a period of weeks. The PFO response to capsules was robust and consistent across all mice tested in this study and previously validated in both non-human primate[43] and human clinical trials[45]. These findings highlight the inventors' platform's ability to increase the local concentration of IL-2 in the IP space for over two weeks without significantly increasing systemic exposure to IL-2. This reduces the clinically relevant concentration needed therapy and thus decreases off-target effects and toxicity. To examine whether the host immune cells were responsible for the PFO on the capsules over time, the inventors implanted immune deficient, NOD-scid IL2Rgamma-null, mice with 200 capsules and explanted them after 14 days. In an immunocompetent mouse, greater than 50% of the implanted capsules were PFO coated at 14 days. However, almost every capsule remained free of PFO and produced approximately the same amount of IL-2 as it did before implantation.

Next, to test the efficacy of this treatment modality in a mouse model of advanced ovarian cancer, female albino mice were injected with ID8/MOSEC cells transduced to express firefly luciferase (ID8 F-Luc) and tumor growth was tracked using luminescent imaging over time. Approximately 90% of ovarian tumors arise from ovarian surface epithelial cells, making ID8/MOSEC murine models a highly relevant testing platform for translational studies[46]. This mouse model has been widely used to study ovarian cancer as well as the effectiveness of immunotherapies and the inventors' knowledge, has yet to been robustly eradicated using a mono immunotherapy[47, 48]. ID8 F-Luc cells were injected into albino mice IP space at a cell density of $1\times10^7$/mouse. Six days post IP injections, animals were randomly stratified into groups and either subjected to a sham surgery or surgically implanted with 10, 50, 100 or 200

RPE-IL2 capsules (each capsule contained approximately $3\times10^4$ RPE-IL2 cells) and tracked with luminescent imagining for 30 days (FIG. 13*a-b*). After only six days of treatment mice with 100 or 200 capsules exhibited a reduction in tumor burden that was 3.3× and 7.5×, respectively, greater than sham mice. After 30 days there was a significant reduction in tumor burden across all groups that received RPE-IL2 capsules. When compared to tumor burden seen in the sham mice, mice with 10, 50, 100 or 200 capsule showed 3.1×, 5×, 53× and 147×, respectively, less tumor burden.

Additionally, an established ID8/MOSEC tumor model was generated and studied to better elucidate the ability of the inventors' therapy to eradicate aggressive cancers as described in figure FIG. 13*c*. Albino mice were injected in the IP space with $1\times10^7$/mouse. Six days post IP injections, animals with a total flux above 1e9 photons/second were stratified into groups, injected with rIL2 for 3 days at a dose of 250,000 IU/day, subjected to a sham surgery, or surgically implanted with either 200 RPE-IL2 or 200 RPE capsules and tracked with luminescent imagining until they reached a total flux of 1e10 photons/second or a humane endpoint (FIGS. 13*d-e*). Total flux from mice that received RPE-IL2 dropped below 5e8 photons/second in less than 1 week of treatment and remained below this threshold for the remained period of the study. All RPE-IL2 mice displayed tumor reduction by at least 90% and 4 of 5 mice showed complete tumor eradication after 15 days and remained tumor free throughout the study Imaging continued until each mouse reached either the flux threshold or clinical endpoint and the resulting survival curve can be seen in (FIG. 13*f*). Survival data for IP models showed the native IL-2 delivered from the capsules had greater potency against IP tumors than the recombinant version of IL-2 when injected on a clinically relevant high dose regimen17, 18. 100% of the RPE-IL2 mice survived significantly longer than the mice in all three of the other groups. None of the mice in this group exhibited tumor growth that passed the initial starting flux. As each mouse reached an endpoint, the animal was sacrificed and the organs (liver, kidney, spleen, uterine horn, IP wall and tumor) were collected and imaged ex vivo (FIG. 12*g*). As seen in the ex vivo organ imaging, mice in the RPE-IL2 group were tumor free across all major organs and no tumor mass was found in the IP space. The mice in each of the other three groups displayed intense tumor burden in each of organs mentioned and showed large tumor masses in the IP space as well as hemoperitoneum and severe organ discoloration. This complete study was repeated with C57BL6 mice at a starting tumor cell dose of 5e6 cells as commonly described in the literature. As seen here, the supplemental studies showed tumor eradication in all 5 RPE-IL2 mice and tumor free IP organs after 70 days. Mice in each of the other three groups showed severe tumor burden in the IP space as well as hemoperitoneum and organ discoloration. These results exhibit clear anti-tumor effects of sustained local delivery of native IL-2 for advanced ovarian cancer.

To confirm their hypothesis that high concentrations of native IL-2 preferentially activate effector T cells (CD8+) and facilitates the perfusion of activated T cells into the tumor space, the inventors conducted an early time-point mechanistic study. As described in FIG. 14*a*, albino mice were injected with $1\times10^7$ cells and stratified into the same experimental groups described in FIGS. 13*a-g*. After 7 days, the mice were sacrificed and the ascites fluid was processed and stained for flow cytometry as described in the methods. Flow cytometry data confirmed a 2× increase in activation (CD25+CD8+) and at least 2× increase in proliferation (Ki67+CD8+) of cytotoxic T cells within the IP space as well as a 3× lower percentage of regulatory T cells (CD4+CD25+FOXp3+) (FIGS. 14*b-d*) in RPE-IL2 treated mice. This study also confirmed a greater than 6× increase in the absolute number of CD4+ as well as a 2× increase in the absolute number of CD8+ T cells in the RPE-IL2 treated mice (FIGS. 14*e-f*). These data suggest that local high concentrations of native IL-2 preferentially active cytotoxic T cells which provides mechanistic insight to why this treatment was so successful in the earlier studies. Of clinical importance, the inventors' platform achieved a 4.5× increase in the effector to suppressive T cell ratio (CD8+/CD4+CD25+FOXp3+). Studies have shown that increases in this ratio correlate with better clinical outcomes (FIG. 14*g*). In a separate study, immune deficient mice were studied to better understand the mechanistic role of native IL-2 on activating immune cells and eliciting anti-tumor effects in vivo.

Following the same experimental conditions listed in FIG. 13*c*, the inventors injected Nu/Nu athymic T cell deficient mice with ID8/MOSEC ovarian cancer cells and administered 200 RPE-IL2 capsules 7 days later. The IVIS luminescent imaging as well as the quantification of total flux over time indicate that high dose native IL-2 treatment does not prevent or even delay tumor growth with the absence of functional T cells (FIGS. 14*h-i*). Similar to the albino groups not treated with RPE-IL2, Nu/nu mice ex vivo organ imaging shows extensive tumor burden on all of the sampled IP organs as well as severe tumor masses in the IP space and along the abdominal wall (FIG. 14*j*) and necropsy imaging show hemoperitoneum, organ discoloration and extensive tumor burden (shown next to an albino mouse treated with 200 RPE-IL2 capsules) (FIG. 14*k*). The data collected from these mechanistic studies confirm the hypothesis that functional T-cells are largely responsible for the anti-tumor effects seen in the ovarian cancer studies with native IL-2 treatment. To test the efficacy of this treatment modality in a mouse model of colorectal cancer, a mix of male and female B6 mice were injected in the IP space with MC38 cells (FIG. 10*a*) at a cell density of $1\times10^6$/mouse. Six days post IP injections, animals were randomly divided into groups and surgically implanted with RPE-IL2 capsules or injected IP with recombinant IL-2 at a dose of 250,000 IU/day for three days and then monitored for seven days. One week after treatment, the mice were sacrificed and the tumors were imaged (FIG. 10*b*) and weighed using an analytical balance. While the average weight of the mice in each of the three groups was similar, there was a significant difference in the weight of the tumors extracted from the mice. No significant loss of body weight or health issues were observed in RPE-IL2 treated groups, suggesting that this treatment was well tolerated in all experimental mice. As shown in (FIG. 10*c*), the tumors in the untreated group as well as the sham surgery group weighed on average 3.1 g and 2.9 g, respectively.

In contrast, the tissue extracted from the RPE-IL2 capsule group did not appear similar in color nor vascularity to the other groups and weighed more than 10× less than the other tumors (FIGS. 15*b*, 15*d*). A survival study was also conducted to study the duration of the anti-tumor affect provided by the RPE-IL2 capsules. A mix of male and female B6 mice were injected in the IP space with MC38 cells at a cell density of $1\times10^6$/mouse. As described above, six days post IP injections, animals were randomly stratified into two groups and either surgically implanted with core shell capsules or subjected to sham surgery. The survival study was terminated eight days after the last sham mouse reached humane endpoint 35 (FIG. 10*c*) and 27 days post injection for RPE-IL2 capsule and sham group, respectively (FIG. 10). At day 35 all RPE-IL2 MC38 injected mice were tumor free.

In a tumor re-challenge study, eight naïve mice and all five of the MC38 tumor free RPE-IL2 mice were injected subcutaneously with 5×105 MC38 cells and monitored until the naïve mice reached critical tumor volume (15 mm diameter) and had to be euthanized After nearly two weeks, none of the five RPE-IL2 mice developed a subcutaneous tumor while five out of the eight naïve mice developed visible tumor just four days post tumor injection (FIG. 10h). These results suggest that in addition to increasing activation and proliferation of CD8+ T cells, RPE-IL2 15 treatment also aids in development of memory T cells that prevent secondary tumors from developing. Further studies need to be executed to confirm this hypothesis. However, these results exhibit clear anti-tumor effects of continuous local delivery of native IL-2 for colorectal cancer. A key design consideration for the RPE-IL2 capsules is their clinical translatability. According to an FDA approved treatment regimen of 600,000 IU/kg, approximately 12 mL or about 6,000 capsules would be needed for a 70 kg patient. IP delivery of anti-cancer agents is a cornerstone in patients with peritoneal metastatic disease, and as such, there are numerous clinically available devices to facilitate IP delivery. To ensure size compatibility of the inventors' capsules with commonly used IP infusion catheters, the inventors benchtop tested the flow of the capsules through a 4 French gauge inner diameter cannula (Accustick II, Boston Scientific). This revealed smooth flow of the capsules without clumping or deformation through the catheter, thus highlighting the immediate clinical translatability of the capsules for IP delivery via a minimally invasive, image-guided procedure. As described above, alginate hydrogels are inert and do not cause adverse health events over time. Similarly, medical devices such as hernia meshes, are permanently implanted. To address variability in the FBR between patients, this approach allows for repeat dose administration if necessary providing clinicians an opportunity to adjust dosing regimens and frequency to achieve best therapeutic outcome patients. Here, the inventors provide evidence that sustained local delivery of native cytokines can be utilized as a monotherapy treatment for multiple metastatic cancers and significantly reduces tumor burden. Local delivery of leukocyte-mimicked native IL-2 from alginate-based microparticles represents a unique platform technology that can be leveraged to continuously deliver various immunotherapeutic molecules in vivo and can be easily scaled up for treatment in humans. The 100-fold concentration difference of IL-2 in blood vs IP space suggests that the inventors' approach may overcome the key toxicity challenges that limited the generality and effectiveness of prior IL-2 therapeutic approaches. Furthermore, control over the number of cells per capsules as well as the number of capsules per dose allows for fine-tuned control of the concentration of IL-2 and serves as a powerful tuning knob for dose adjustment based on the patient prognosis information. At low concentrations, IL-2 recruits regulatory T-cells and is immunosuppressive. This means that this "cytokine factory" approach to IL-2 therapy is a significantly more robust approach than conventional injection of recombinant IL-2. The tight autonomous guard banding of IP therapeutic concentrations is a unique feature of the inventors' encapsulated cell therapy platform, which is qualitatively not achievable by biologic injections. Importantly, this technology could enable the exploration and use of therapeutic lead candidates with significant toxicity at very narrow concentration windows where they are both safe and effective. In the near-term this treatment has the potential to greatly affect the outlook of ovarian cancer patients with platinum 20 resistant tumors who currently expect no more 12 months median survival based on available therapies.

The cytokines delivered in this study represent example therapeutics, but any number or combination of immunotherapeutic molecules can be substituted to create a personalized immunotherapy. The plug and play cell engineering platform described here enables rapid development of novel cytokine therapeutics with similar pharmacokinetics without the need for cumbersome protein engineering nor extended release formulation development. Future work will be focused on combining cytokine delivery with immune checkpoint inhibitors such as PD-1 and CTLA-4 to create immunotherapeutic cocktails that can be carefully tailored for various cancers and tumor severities50. Alginate-based encapsulation systems for delivery of native IL-2 as a successful monotherapy for metastatic cancers is a starting point for encapsulated cell therapies and is essentially only limited by the size of the pores restricting efficient diffusion into the surrounding space. Pro-inflammatory cytokines are used in this work, but this platform technology can also be used to deliver anti-inflammatory molecules, such as IL-10, to address a wide array of immunological disorders including osteoarthritis, inflammatory bowel disease, and type 1 diabetes.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. An implantable construct comprising:
    (i) an inner alginate layer encapsulating a a plurality of retinal epithelial pigment cells expressing human IL-2,
    (ii) an outer alginate layer,
    wherein the implantable construct:
    is configured for implantation into the intraperitoneal space or the pleural cavity of a subject, and
    is further configured to provide a first release phase wherein the rate of release of the human IL-2 is substantially constant and a second release phase wherein the level of release of the human IL-2 is substantially declining.

2. The implantable construct of claim 1, wherein the plurality of retinal epithelial pigment cells are ARPE-19 cells.

3. The implantable construct of claim 1, wherein the plurality of retinal epithelial pigment comprises greater than about 1000 cells expressing IL-2.

4. The intraperitoneal space implantable construct of claim 1, wherein the plurality of retinal epithelial pigment comprises greater than about 1000 cells expressing IL-2 and less than $1\times10^5$ expressing IL-2 cells.

5. The implantable construct of claim 1, wherein the implantable construct secretes IL-2 for about 4 weeks when implanted in a subject.

6. The implantable construct of claim 1, wherein the implantable construct has a decrease in function about 2 weeks after implantation in the subject.

7. The intraperitoneal space implantable construct of claim 6, wherein the decrease in function is a decrease in secretion of the IL-2.

8. The implantable construct of claim 1, wherein the implantable construct becomes fibrosed after implantation in a subject.

9. The implantable construct of claim 1, wherein the implantable construct does not comprise an antifibrotic feature.

10. A method of treating cancer or reducing tumor size in a subject, the method comprising implanting into the intraperitoneal space or the pleural cavity of a subject the implantable construct of claim 1.

11. The method of claim 10, wherein the concentration of the secreted IL-2 in the intraperitoneal space of the subject is 2-fold or more than the concentration of the secreted IL-2 in the blood of the subject when the implantable construct is implanted in the intraperitoneal space.

12. The method of claim 10, wherein the concentration of the secreted IL-2 in the intraperitoneal space of the subject is 50-fold or more than the concentration of the secreted IL-2 in the blood of the subject when the implantable construct is implanted in the intraperitoneal space.

13. The method of claim 10, wherein the concentration of the secreted IL-2 in the intraperitoneal space of the subject is 50-fold or more than the concentration of the secreted IL-2 in the blood of the subject for at least 6 days after implantation in the intraperitoneal space.

14. The method of claim 10, wherein the implantable construct does not comprise an antifibrotic feature.

15. The implantable construct of claim 1, wherein the implantable construct is coated with fibrotic overgrowth after being implanted in the subject.

16. The implantable construct of claim 1, wherein fibrotic overgrowth causes a decrease in function of the implantable construct about 2 weeks after implantation in the subject.

17. The method of claim 10, wherein the cancer is pancreatic cancer or melanoma, or the tumor is a pancreatic tumor or melanoma.

18. The method of claim 10, wherein the concentration of the secreted IL-2 in the intraperitoneal space decreases between 2 and 4 weeks after implantation in the intraperitoneal space.

19. The method of claim 10, wherein the implantation of the implantable construct produces an upregulation in T effector cells.

20. The method of claim 19, wherein the implantation does not activate a T regulator cell in the subject.

21. The implantable construct of claim 1, wherein the implantable construct has a mean diameter size of 1 mm or larger.

22. The implantable construct of claim 1, and wherein the implantable construct comprises a sphere.

* * * * *